United States Patent
Wu et al.

(10) Patent No.: US 8,643,001 B2
(45) Date of Patent: *Feb. 4, 2014

(54) SEMICONDUCTOR COMPOSITION

(75) Inventors: Yiliang Wu, Oakville (CA); Anthony James Wigglesworth, Oakville (CA); Ping Liu, Mississauga (CA); Nan-Xing Hu, Oakville (CA)

(73) Assignee: Samsung Electronics Co. Ltd., Gyeonggi-do (KR)

( * ) Notice: Subject to any disclaimer, the term of this patent is extended or adjusted under 35 U.S.C. 154(b) by 260 days.

This patent is subject to a terminal disclaimer.

(21) Appl. No.: 12/977,464

(22) Filed: Dec. 23, 2010

(65) Prior Publication Data

US 2012/0161110 A1    Jun. 28, 2012

(51) Int. Cl.
*H01L 51/30* (2006.01)

(52) U.S. Cl.
USPC .................................................. 257/40; 59/72

(58) Field of Classification Search
USPC ............................................. 257/40, 59, 72
See application file for complete search history.

(56) References Cited

U.S. PATENT DOCUMENTS

| | | | |
|---|---|---|---|
| 8,283,660 B2 * | 10/2012 | Wigglesworth et al. | 257/40 |
| 2010/0176376 A1 | 7/2010 | Suzuki et al. | |
| 2010/0219404 A1 | 9/2010 | Endo et al. | |
| 2011/0073854 A1 | 3/2011 | Moriwaki et al. | |

* cited by examiner

*Primary Examiner* — Robert D. Harlan
(74) *Attorney, Agent, or Firm* — Harness, Dickey & Pierce, P.L.C.

(57) ABSTRACT

An electronic device, such as a thin-film transistor, includes a semiconducting layer formed from a semiconductor composition. The semiconductor composition comprises a polymer binder and a small molecule semiconductor of Formula (I):

Formula (I)

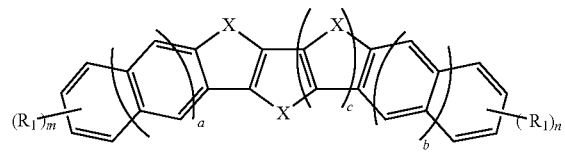

wherein $R_1$, m, n, a, b, c, and X are as described herein. Devices formed from the composition exhibit high mobility and excellent stability.

20 Claims, 6 Drawing Sheets

SEMICONDUCTOR COMPOSITION

BACKGROUND

The present disclosure relates to thin-film transistors (TFTs) and/or other electronic devices comprising a semiconducting layer. The semiconducting layer is formed from a semiconductor composition as described herein. When the composition is used in the semiconducting layer of a device, high mobility and excellent stability may be achieved.

TFTs are generally composed of, on a substrate, an electrically conductive gate electrode, source and drain electrodes, an electrically insulating gate dielectric layer which separate the gate electrode from the source and drain electrodes, and a semiconducting layer which is in contact with the gate dielectric layer and bridges the source and drain electrodes. Their performance can be determined by the field effect mobility and the current on/off ratio of the overall transistor. High mobility and high on/off ratio are desired.

Organic thin-film transistors (OTFTs) can be used in applications such as radio frequency identification (RFID) tags and backplane switching circuits for displays, such as signage, readers, and liquid crystal displays, where high switching speeds and/or high density are not essential. They also have attractive mechanical properties such as being physically compact, lightweight, and flexible.

Organic thin-film transistors can be fabricated using low-cost solution-based patterning and deposition techniques, such as spin coating, solution casting, dip coating, stencil/screen printing, flexography, gravure, offset printing, ink jet-printing, micro-contact printing, and the like. To enable the use of these solution-based processes in fabricating thin-film transistor circuits, solution processable materials are therefore required. However, organic or polymeric semiconductors formed by solution processing tend to suffer from limited solubility, air sensitivity, and especially low field-effect mobility. This poor performance may be attributable to the poor film-forming nature of small molecules.

It would be desirable to develop a semiconducting composition that exhibits high field effect mobility and good film-forming properties.

BRIEF DESCRIPTION

The present application discloses, in various embodiments, electronic devices, semiconductor compositions used in the electronic devices, and processes for making such electronic devices. The semiconducting layer is formed from a semiconductor composition that comprises a polymer binder and a small molecule semiconductor of Formula (I):

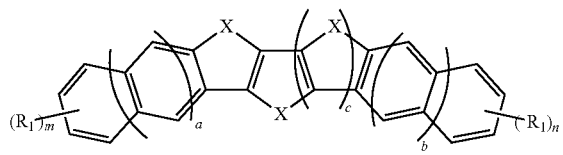

Formula (I)

wherein each $R_1$ is independently selected from alkyl, substituted alkyl, alkenyl, substituted alkenyl, alkynyl, substituted alkynyl, aryl, substituted aryl, heteroaryl, substituted heteroaryl, alkoxy, alkylthio, trialkylsilyl, ketonyl, cyano, and halogen; m and n are the number of $R_1$ sidechains on their respective phenyl or naphthyl ring, and are independently an integer from 0 to 6; X is selected from the group consisting of O, S, and Se; and a, b, and c are independently 0 or 1. The resulting semiconducting layer achieves high mobility and has excellent stability. The electronic device comprises a semiconducting layer formed from such a semiconductor composition. In embodiments, the electronic devices are thin-film transistors.

Disclosed in embodiments is a semiconductor composition comprising: a polymer binder; and a small molecule semiconductor of Formula (I):

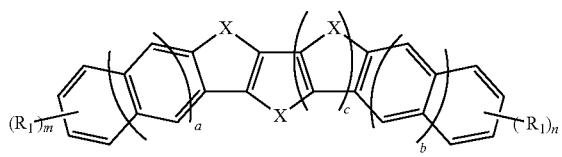

Formula (I)

wherein each $R_1$ is independently selected from alkyl, substituted alkyl, alkenyl, substituted alkenyl, alkynyl, substituted alkynyl, aryl, substituted aryl, heteroaryl, substituted heteroaryl, alkoxy, alkylthio, trialkylsilyl, ketonyl, cyano, and halogen; m and n are the number of $R_1$ sidechains on their respective phenyl or naphthyl ring, and are independently an integer from 0 to 6; X is selected from the group consisting of O, S, and Se; and a, b, and c are independently 0 or 1. The semiconductor composition is capable of forming a semiconductor layer having a field-effect mobility greater than 0.10 $cm^2/V \cdot sec$.

In particular embodiments, the small molecule semiconductor has the structure of Formula (II):

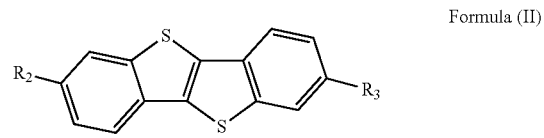

Formula (II)

wherein $R_2$ and $R_3$ are independently selected from alkenyl, substituted alkenyl, alkynyl, substituted alkynyl, aryl, substituted aryl, heteroaryl, substituted heteroaryl, alkoxy, alkylthio, trialkylsilyl, ketonyl, cyano, and halogen.

The polymer binder may be a styrene-based polymer or an arylamine-based polymer. In particular, the polymer binder can be a homopolymer or a copolymer. In some specific embodiments, the polymer binder is polystyrene, poly(α-methyl styrene), poly(4-methyl styrene), poly(alpha-methyl styrene-co-vinyl toluene), poly(styrene-block-butadiene-block-styrene), poly(styrene-block-isopene-block-styrene), poly(vinyl toluene), a terpene resin, poly(styrene-co-2,4-dimethylstyrene), poly(chlorostyrene), poly(styrene-co-α-methyl styrene), poly(styrene-co-butadiene), polycarbazole, a polytriarylamine, or poly(N-vinylcarbazole). In particular embodiments, the polymer binder is a styrene-based polymer having a weight average molecular weight of from about 40,000 to about 2,000,000.

The polymer binder, in some embodiments, has a dielectric constant less than 3.5.

In other embodiments, the small molecule semiconductor has the structure of Formula (II):

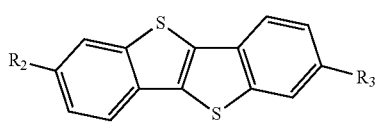

Formula (II)

wherein $R_2$ and $R_3$ are independently alkyl or substituted alkyl; and wherein the polymer binder is a styrene-based polymer or an arylamine-based polymer.

In specific embodiments of the semiconductor composition containing the compound of Formula (II), the polymer binder is polystyrene, poly(α-methyl styrene), poly(4-methyl styrene), poly(alpha-methyl styrene-co-vinyl toluene), polystyrene-block-butadiene-block-styrene), poly(styrene-block-isoprene-block-styrene), poly(vinyl toluene), a terpene resin, poly(styrene-co-2,4-dimethylstyrene), poly(chlorostyrene), poly(styrene-co-α-methyl styrene), poly(styrene-co-butadiene), polycarbazole, a polytriarylamine, or poly(N-vinylcarbazole). In other embodiments, the polymer binder is a styrene-based polymer having a weight average molecular weight of from about 100,000 to about 1,000,000.

In other embodiments, the small molecule semiconductor has the structure of Formula (III):

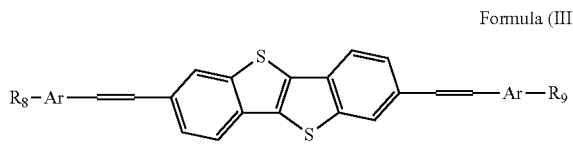

Formula (III)

wherein $R_8$, and $R_9$ are independently alkyl or substituted alkyl; and each Ar is independently an arylene or heteroarylene group.

In other embodiments, the small molecule semiconductor is selected from Formulas (1) through (50), shown further herein, wherein each R' is independently alkyl or substituted alkyl containing from about 4 to about 20 carbon atoms.

In yet other embodiments, the small molecule semiconductor has the structure of Formula (IV):

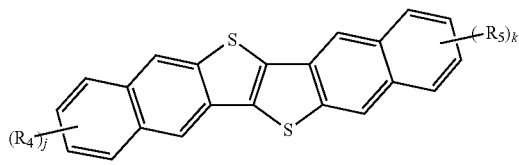

Formula (IV)

wherein $R_4$ and $R_5$ are independently selected from alkyl, substituted alkyl, alkenyl, substituted alkenyl, alkynyl, substituted alkynyl, aryl, substituted aryl, heteroaryl, substituted heteroaryl, alkoxy, alkylthio, trialkylsilyl, ketonyl, cyano, and halogen; and j and k are independently an integer from 0 to 6.

In some embodiments, $R_4$ and $R_5$ are the same. In others, $R_4$ and $R_5$ are independently alkyl, j is 1, and k is 1.

In particular embodiments of the semiconductor composition containing the compound of Formula (IV), the polymer binder is a styrene-based polymer or an arylamine-based polymer.

In specific embodiments, the weight ratio of the small molecule semiconductor of Formula (I) to the polymer binder is from about 5:1 to about 2:3, and the total amount of the small molecule semiconductor and the polymer binder is from about 0.1 to about 10 weight percent of the semiconductor composition.

In other embodiments, the small molecule semiconductor has the structure of Formula (V):

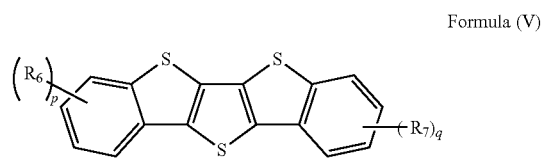

Formula (V)

wherein $R_6$ and $R_7$ are independently selected from alkyl, substituted alkyl, alkenyl, substituted alkenyl, alkynyl, substituted alkynyl, aryl, substituted aryl, heteroaryl, substituted heteroaryl, alkoxy, alkylthio, trialkylsilyl, ketonyl, cyano, and halogen; and p and q are independently an integer from 0 to 4.

In some embodiments, the small molecule semiconductor has the structure of Formula (VI):

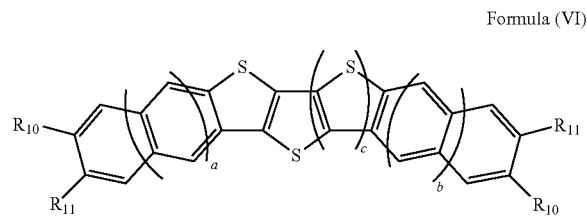

Formula (VI)

wherein $R_{10}$ and $R_{11}$ are independently selected from alkyl, substituted alkyl, alkenyl, substituted alkenyl, alkynyl, substituted alkynyl, aryl, substituted aryl, heteroaryl, substituted heteroaryl, alkoxy, alkylthio, trialkylsilyl, ketonyl, cyano, and halogen; and a, b, and c are independently 0 or 1.

Also disclosed herein is a process for making a semiconducting layer of an electronic device. A composition is deposited upon a surface. The composition comprises a polymer binder and a small molecule semiconductor of Formula (I):

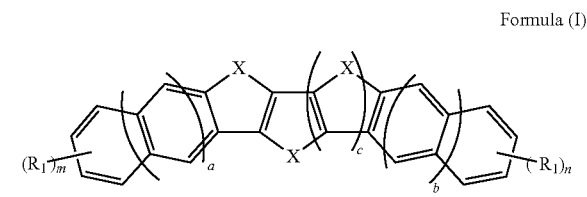

Formula (I)

wherein each $R_1$ is independently selected from alkyl, substituted alkyl, alkenyl, substituted alkenyl, alkynyl, substituted alkynyl, aryl, substituted aryl, heteroaryl, substituted heteroaryl, alkoxy, alkylthio, trialkylsilyl, ketonyl, cyano, and halogen; m and n are the number of $R_1$ sidechains on their respective phenyl or naphthyl ring, and are independently an integer from 0 to 6; X is selected from the group consisting of O, S, and Se; and a, b and c are independently 0 or 1. Next, the composition is dried and then optionally annealed at a temperature below the melting point of the small molecular semiconductor to form the semiconducting layer. The semiconducting layer has a mobility of at least 0.10 cm²/V·sec.

Also disclosed is an electronic device comprising a semiconducting layer, wherein the semiconducting layer comprising a polymer binder and a small molecule semiconductor of Formula (I):

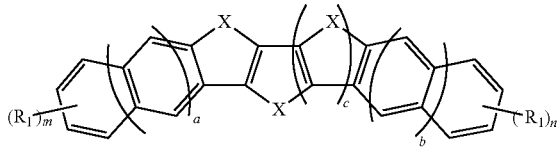

Formula (I)

wherein each $R_1$ is independently selected from alkyl, substituted alkyl, alkenyl, substituted alkenyl, alkynyl, substituted alkynyl, aryl, substituted aryl, heteroaryl, substituted heteroaryl, alkoxy, alkylthio, trialkylsilyl, ketonyl, cyano, and halogen; m and n are the number of $R_1$ sidechains on their respective phenyl or naphthyl ring, and are independently an integer from 0 to 6; X is selected from the group consisting of O, S, and Se; and a, b and c are independently 0 or 1; wherein the semiconducting layer has a field-effect mobility of at least 0.10 cm²/V·sec. Specifically, the electronic device is a thin film transistor.

The polymer binder may be a styrene-based polymer or an arylamine-based polymer.

The electronic device may further comprise a dielectric layer, wherein the dielectric layer comprises a modified surface. The semiconducting layer is in direct contact with the modified surface. In some embodiments, the surface has been modified with a polystyrene, a polysiloxane, a polysilsesquioxane, or an organosilane agent of Formula (A):

Formula (A)

wherein R is hydrocarbon or fluorocarbon containing from 1 to about 20 carbon atoms, R" is halogen or alkoxy; and m is an integer from 1 to 4.

The electronic device may have a mobility of at least 0.4 cm²/V·sec; and/or a current on/off ratio of at least $10^5$.

These and other non-limiting characteristics of the disclosure are more particularly disclosed below.

BRIEF DESCRIPTION OF THE DRAWINGS

The following is a brief description of the drawings, which are presented for the purposes of illustrating the exemplary embodiments disclosed herein and not for the purposes of limiting the same.

DETAILED DESCRIPTION

Figure 1:
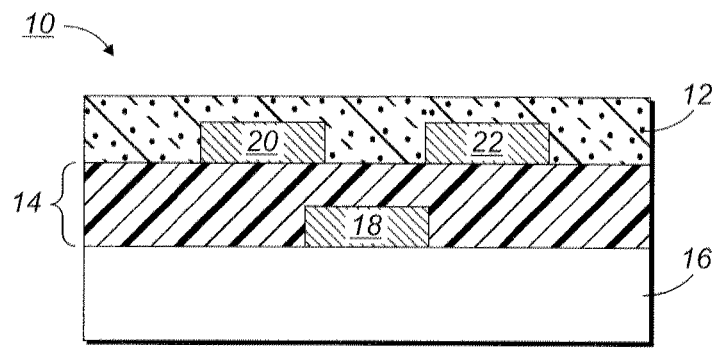
FIG. 1 is a diagram of a first embodiment of a TFT according to the present disclosure.

A more complete understanding of the components, processes and apparatuses disclosed herein can be obtained by reference to the accompanying drawings. These figures are merely schematic representations based on convenience and the ease of demonstrating the present disclosure, and are, therefore, not intended to indicate relative size and dimensions of the devices or components thereof and/or to define or limit the scope of the exemplary embodiments.

Although specific terms are used in the following description for the sake of clarity, these terms are intended to refer only to the particular structure of the embodiments selected for illustration in the drawings, and are not intended to define or limit the scope of the disclosure. In the drawings and the following description below, it is to be understood that like numeric designations refer to components of like function.

The modifier "about" used in connection with a quantity is inclusive of the stated value and has the meaning dictated by the context (for example, it includes at least the degree of error associated with the measurement of the particular quantity). When used in the context of a range, the modifier "about" should also be considered as disclosing the range defined by the absolute values of the two endpoints. For example, the range of "from about 2 to about 10" also discloses the range "from 2 to 10."

The term "comprising" is used herein as requiring the presence of the named component and allowing the presence of other components. The term "comprising" should be construed to include the term "consisting of", which allows the presence of only the named component, along with any impurities that might result from the manufacture of the named component.

The present disclosure relates to a composition comprising a polymer binder and a small molecule semiconductor as described further herein. A semiconducting layer formed from the composition is very stable in air and has high mobility. These semiconductor compositions are useful for forming layers in electronic devices, such as thin film transistors (TFTs). The semiconductor composition is capable of forming a layer having a field-effect mobility greater than 0.10 cm²/V·sec, including greater than 0.15 cm²/V·sec.

FIG. 1 illustrates a bottom-gate bottom-contact TFT configuration according to the present disclosure. The TFT 10 comprises a substrate 16 in contact with the gate electrode 18 and a gate dielectric layer 14. The gate electrode 18 is depicted here atop the substrate 16, but the gate electrode could also be located in a depression within the substrate. It is important that the gate dielectric layer 14 separates the gate electrode 18 from the source electrode 20, drain electrode 22, and the semiconducting layer 12. The semiconducting layer 12 runs over and between the source and drain electrodes 20 and 22. The semiconductor has a channel length between the source and drain electrodes 20 and 22.

Figure 2:
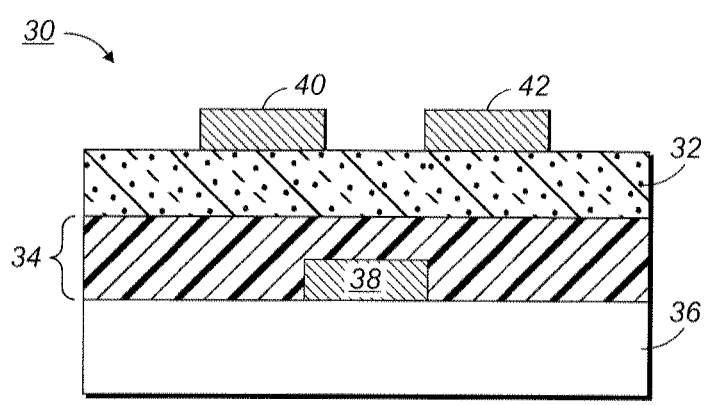
FIG. 2 is a diagram of a second embodiment of a TFT according to the present disclosure.

FIG. 2 illustrates another bottom-gate top-contact TFT configuration according to the present disclosure. The TFT 30 comprises a substrate 36 in contact with the gate electrode 38 and a gate dielectric layer 34. The semiconducting layer 32 is placed on top of the gate dielectric layer 34 and separates it from the source and drain electrodes 40 and 42.

Figure 3:
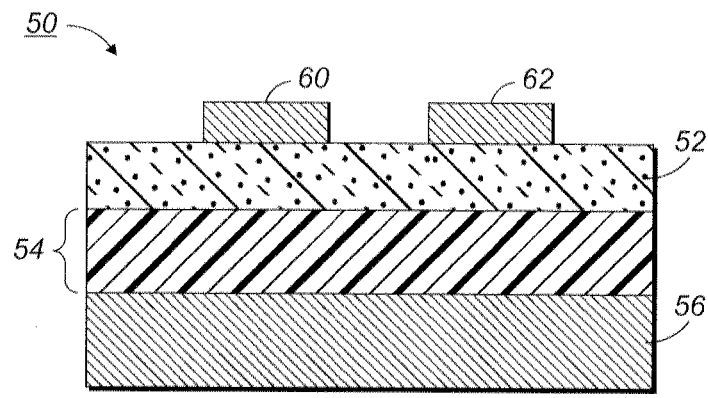
FIG. 3 is a diagram of a third embodiment of a TFT according to the present disclosure.

FIG. 3 illustrates a bottom-gate bottom-contact TFT configuration according to the present disclosure. The TFT 50 comprises a substrate 56 which also acts as the gate electrode and is in contact with a gate dielectric layer 54. The source electrode 60, drain electrode 62, and semiconducting layer 52 are located atop the gate dielectric layer 54.

Figure 4:
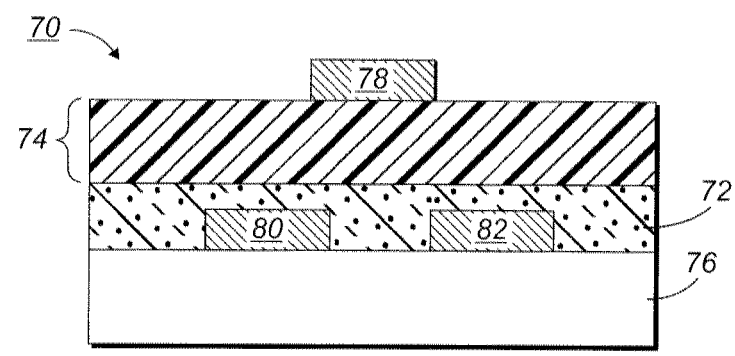
FIG. 4 is a diagram of a fourth embodiment of a TFT according to the present disclosure.

FIG. 4 illustrates a top-gate top-contact TFT configuration according to the present disclosure. The TFT 70 comprises a substrate 76 in contact with the source electrode 80, drain electrode 82, and the semiconducting layer 72. The semiconducting layer 72 runs over and between the source and drain electrodes 80 and 82. The gate dielectric layer 74 is on top of the semiconducting layer 72. The gate electrode 78 is on top of the gate dielectric layer 74 and does not contact the semiconducting layer 72.

The semiconductor composition comprises a polymer binder and a small molecule semiconductor. The small molecule semiconductor has the structure of Formula (I):

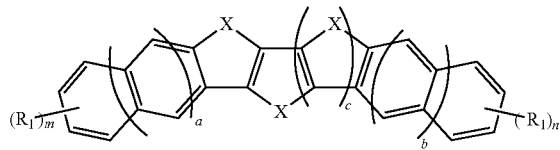

Formula (I)

wherein each $R_1$ is independently selected from alkyl, substituted alkyl, alkenyl, substituted alkenyl, alkynyl, substituted alkynyl, aryl, substituted aryl, heteroaryl, substituted heteroaryl, alkoxy, alkylthio, trialkylsilyl, ketonyl, cyano (CN), and halogen; m and n are the number of $R_1$ sidechains on their respective phenyl or naphthyl ring, and are independently an integer from 0 to 6; X is selected from the group consisting of O, S, and Se; and a, b, and c are independently 0 or 1. In this regard, when a or b is 0, the exterior portion of the compound will be a phenyl ring that may have up to 4 sidechains. When a or b is 1, the exterior portion of the compound will be a naphthyl ring that may have up to 6 sidechains.

The term "alkyl" refers to a radical composed entirely of carbon atoms and hydrogen atoms which is fully saturated and of the formula $-C_nH_{2n+1}$. The alkyl radical may be linear, branched, or cyclic.

The term "alkenyl" refers to a radical composed entirely of carbon atoms and hydrogen atoms which contains at least one carbon-carbon double bond that is not part of an aryl or heteroaryl structure. The radical may be linear, branched, or cyclic.

The term "alkynyl" refers to a radical composed entirely of carbon atoms and hydrogen atoms which contains at least one carbon-carbon triple bond. The alkynyl radical may be linear, branched, or cyclic.

The term "aryl" refers to an aromatic radical composed entirely of carbon atoms and hydrogen atoms. When aryl is described in connection with a numerical range of carbon atoms, it should not be construed as including substituted aromatic radicals. For example, the phrase "aryl containing from 6 to 10 carbon atoms" should be construed as referring to a phenyl group (6 carbon atoms) or a naphthyl group (10 carbon atoms) only, and should not be construed as including a methylphenyl group (7 carbon atoms).

The term "heteroaryl" refers to an aromatic radical composed of carbon atoms, hydrogen atoms, and one or more heteroatoms. The carbon atoms and the heteroatoms are present in a cyclic ring or backbone of the radical. The heteroatoms are selected from O, S, and N. Exemplary heteroaryl radicals include thienyl and pyridinyl.

The term "alkoxy" refers to an alkyl radical which is attached to an oxygen atom, i.e. $-O-C_nH_{2n+1}$.

The term "alkylthio" refers to an alkyl radical which is attached to a sulfur atom, i.e. $-S-C_nH_{2n+1}$.

The term "trialkylsilyl" refers to a radical composed of a tetravalent silicon atom having three alkyl radicals attached to the silicon atom, i.e. $-Si(R)_3$. The three alkyl radicals may be the same or different.

The term "ketonyl" refers to a radical having a carbon atom double-bonded to an oxygen atom and single bonded to an alkyl or substituted alkyl group, i.e. $-(C=O)-R$. An exemplary ketonyl radical is methylcarbonyl ($-COCH_3$).

The term "substituted" refers to at least one hydrogen atom on the named radical being substituted with another functional group, such as halogen, $-CN$, $-NO_2$, $-COOH$, and $-SO_3H$. An exemplary substituted alkyl group is a perhaloalkyl group, wherein one or more hydrogen atoms in an alkyl group are replaced with halogen atoms, such as fluorine, chlorine, iodine, and bromine. Besides the aforementioned functional groups, an aryl or heteroaryl group may also be substituted with alkyl or alkoxy. Exemplary substituted aryl groups include methylphenyl and methoxyphenyl. Exemplary substituted heteroaryl groups include dodecylthienyl.

Generally, the alkyl and alkoxy groups each independently contain from 1 to 30 carbon atoms, including from about 4 to about 16 carbon atoms. Similarly, the aryl groups independently contain from 6 to 30 carbon atoms.

When a, b, and c are 0, the molecule of Formula (I) is also formally known as a disubstituted-[2]benzothieno[3,2-b]benzothiophene. The [1]benzothieno[3,2-b]benzothiophene moiety may be abbreviated herein as "BTBT". For example, the semiconductor of Formula (I) could be referred to as a disubstituted-BTBT.

In embodiments, the small molecule semiconductor has a band gap of from about 1.5 to about 3.5 eV, including from about 1.8 to about 2.8 eV. This large band gap typically means that the small molecule semiconductor has better stability in air, when compared to a pentacene-based semiconductor. The small molecule semiconductor has a crystalline or liquid crystalline structure. In specific embodiments, the semiconductor of Formula (I) is colorless in the visible region of the electromagnetic spectrum (i.e. from 390 nm to 750 nm). Colorless semiconductors not only provide excellent stability due to their large band gaps, but also offer advantage in transparency for transparent device applications.

Five particular variations of the compound of Formula (I) are contemplated by the present disclosure. In one variation, the small molecule semiconductor has the structure of Formula (II):

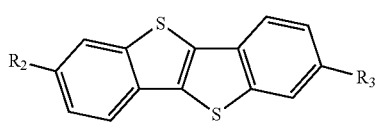

Formula (II)

wherein $R_2$ and $R_3$ are independently selected from alkyl, substituted alkyl, alkenyl, substituted alkenyl, alkynyl, substituted alkynyl, aryl, substituted aryl, heteroaryl, substituted heteroaryl, alkoxy, alkylthio, trialkylsilyl, ketonyl, cyano, and halogen. On this semiconductor compound of Formula (II), $R_2$ is located at the 2-position and $R_3$ is located at the 7-position. Thus, the compound of Formula (II) could be referred to as a 2,7-disubstituted-BTBT. Referring to Formula (I), the compound of Formula (II) is obtained when a, b, and c are 0.

In some embodiments, the $R_2$ and $R_3$ are independently selected from alkenyl, substituted alkenyl, alkynyl, substituted alkynyl, aryl, substituted aryl, heteroaryl, substituted heteroaryl, alkoxy, alkylthio, trialkylsilyl, ketonyl, cyano, and halogen. In some other embodiments, $R_2$ and $R_3$ are independently selected from alkyl and substituted alkyl, and the small molecule semiconductor is combined with specific polymer binders to achieve high field-effect mobility. The polymer binders will be explained further herein. The alkyl group may contain from about 4 to about 30 carbon atoms, including from about 4 to about 16 carbon atoms. Exemplary alkyl groups include butyl, pentyl, hexyl, heptyl, octyl, decyl, dodecyl, tridecyl, hexadecyl, and the like. In some embodiments, the alkyl group has an odd number of carbon atoms; in other embodiments the alkyl group has an even number of carbon atoms. In particular embodiments, $R_2$ and $R_3$ are the same.

In another variation, the small molecule semiconductor has the structure of Formula (III):

Formula (III)

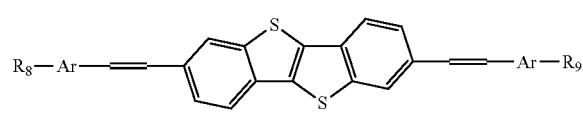

wherein $R_8$, and $R_9$ are independently alkyl or substituted alkyl; and each Ar is independently an arylene or heteroarylene group. Referring again to Formula (I), the compound of Formula (III) is obtained when a, b, and c are 0; m and n are 1; and each $R_1$ is alkenyl or substituted alkenyl. The alkyl group may contain from 1 to about 30 carbon atoms, including from about 4 to about 18 carbon atoms.

The term "arylene" refers to an aromatic radical composed entirely of carbon atoms and hydrogen atoms that can form single bonds with two different atoms. An exemplary arylene group is phenylene (—$C_6H_4$—).

The term "heteroarylene" refers to an aromatic radical composed of carbon atoms, hydrogen atoms, and one or more heteroatoms, and that can form single bonds with two different atoms. The carbon atoms and the heteroatoms are present in a cyclic ring or backbone of the radical. The heteroatoms are selected from O, S, and N. An exemplary heteroarylene group is 2,5-thienyl.

In a third variation, the small molecule semiconductor has the structure of Formula (IV):

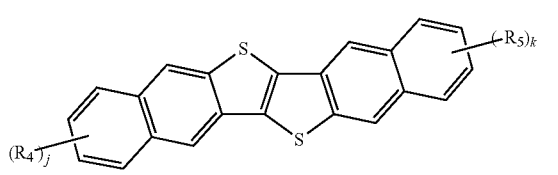

Formula (IV)

wherein $R_4$ and $R_5$ are independently selected from alkyl, substituted alkyl, alkenyl, substituted alkenyl, alkynyl, substituted alkynyl, aryl, substituted aryl, heteroaryl, substituted heteroaryl, alkoxy, alkylthio, trialkylsilyl, ketonyl, cyano, and halogen; and j and k are independently an integer from 0 to 6. Referring again to Formula (I), the compound of Formula (IV) is obtained when a and b are both 1, and c is 0. The $R_4$ and $R_5$ sidechains may be located on any carbon atom of the exterior naphthyl portions of the compound of Formula (IV).

In specific embodiments of Formula (IV), $R_4$ and $R_5$ are independently alkyl, j is 1, and k is 1.

In the next variation, the small molecule semiconductor has the structure of Formula (V):

Formula (V)

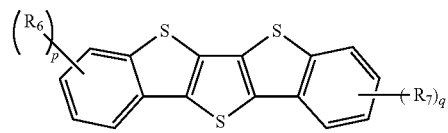

wherein $R_6$ and $R_7$ are independently selected from alkyl, substituted alkyl, alkenyl, substituted alkenyl, alkynyl, substituted alkynyl, aryl, substituted aryl, heteroaryl, substituted heteroaryl, alkoxy, alkylthio, trialkylsilyl, ketonyl, cyano, and halogen; and p and q are independently an integer from 0 to 4. Referring again to Formula (I), the compound of Formula (V) is obtained when a and b are both 0, and c is 1.

In the final variation, the small molecule semiconductor has the structure of Formula (VI):

Formula (VI)

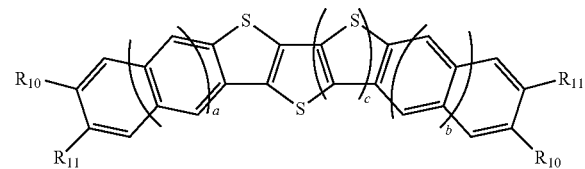

wherein $R_{10}$ and $R_{11}$ are independently selected from alkyl, substituted alkyl, alkenyl, substituted alkenyl, alkynyl, substituted alkynyl, aryl, substituted aryl, heteroaryl, substituted heteroaryl, alkoxy, alkylthio, trialkylsilyl, ketonyl, cyano, and halogen; and a, b, and c are independently 0 or 1.

In particular embodiments of Formula (VI), $R_{10}$ is halogen or cyano, and $R_{11}$ is alkyl, substituted alkyl, alkenyl, substituted alkenyl, or ketonyl. In other embodiments, $R_{11}$ is halogen or cyano, and $R_{10}$ is alkyl, substituted alkyl, alkenyl, substituted alkenyl, or ketonyl.

Other specific variations on the small molecule semiconductor of Formula (I) are also shown here as Formulas (1)-(50):

Formula (1)
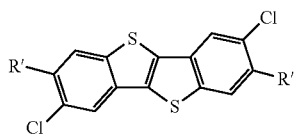
Formula (2)
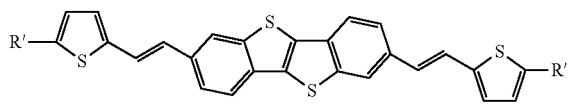
Formula (3)
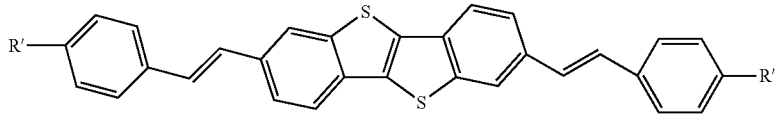
Formula (4)
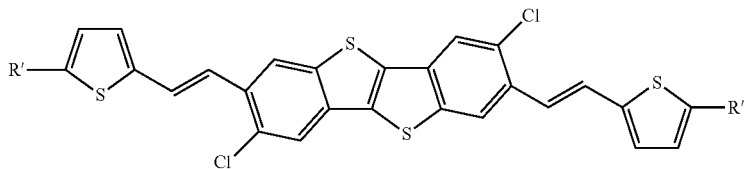
Formula (5)
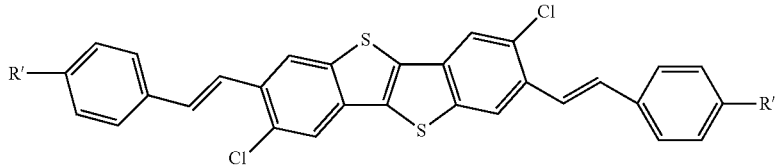
Formula (6)
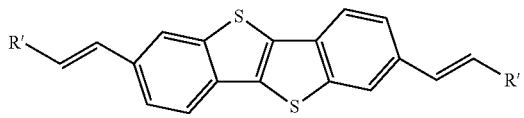
Formula (7)
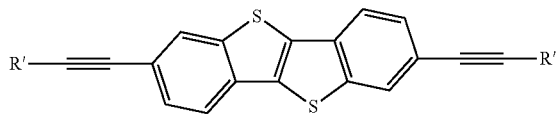
Formula (8)
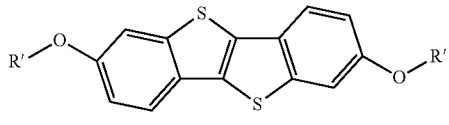
Formula (9)
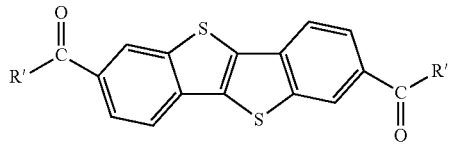
Formula (10)
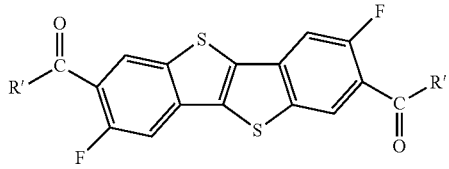
Formula (11)
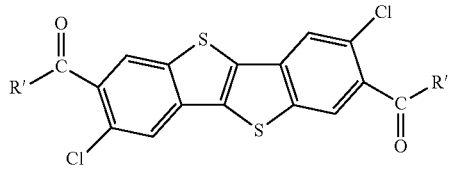
Formula (12)
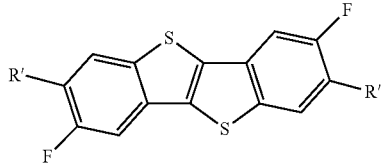
Formula (13)
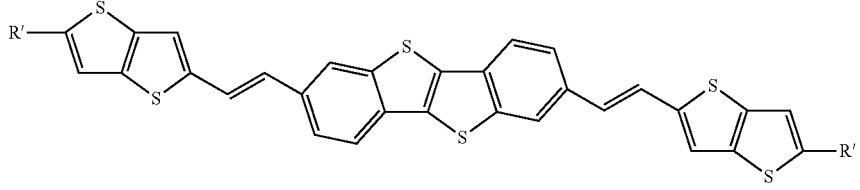

-continued
Formula (14)
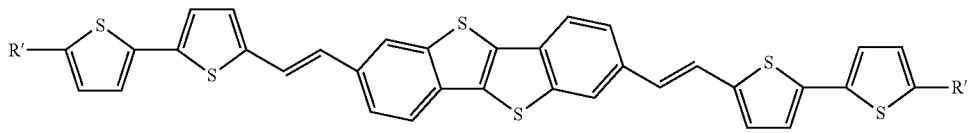
Formula (15)
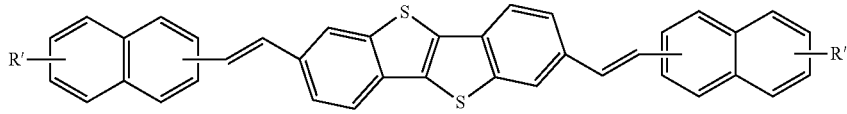
Formula (16)
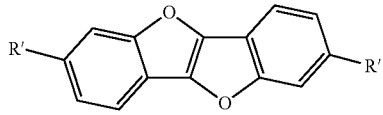
Formula (17)
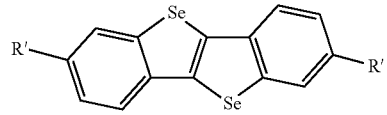
Formula (18)
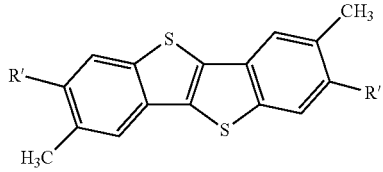
Formula (19)
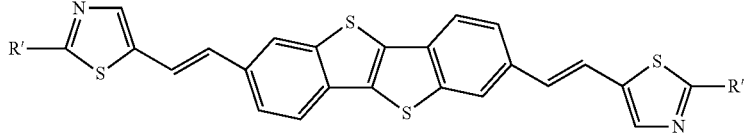
Formula (20)
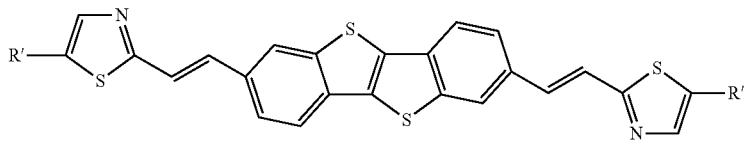
Formula (21)
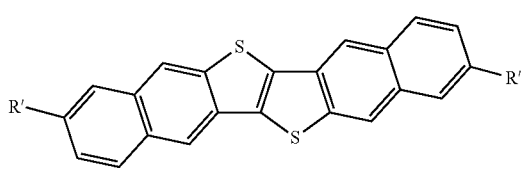
Formula (22)
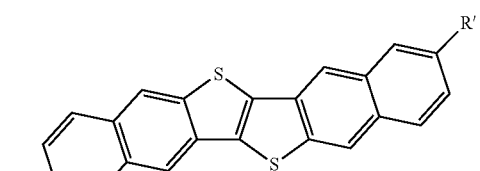
Formula (23)
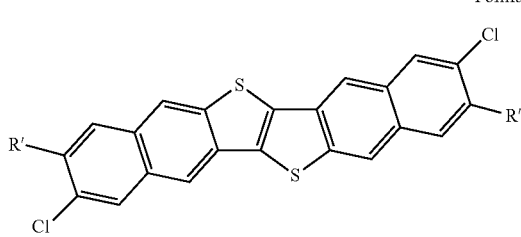
Formula (24)
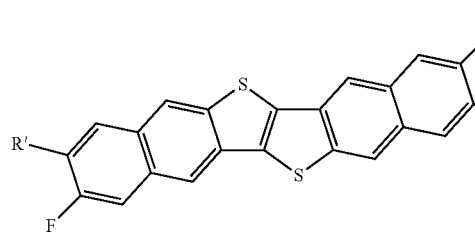
Formula (25)
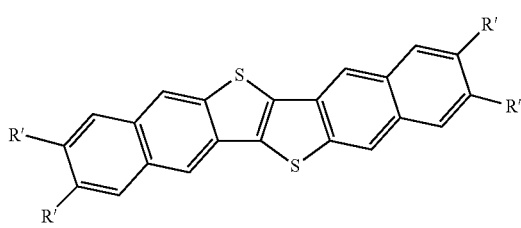
Formula (26)
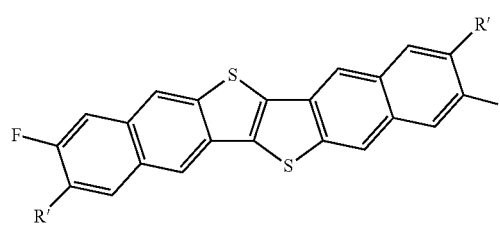
Formula (27)

Formula (28)
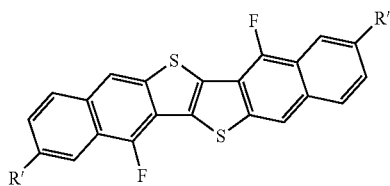
Formula (29)
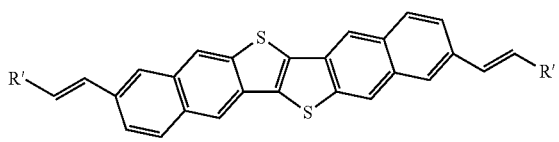
Formula (30)
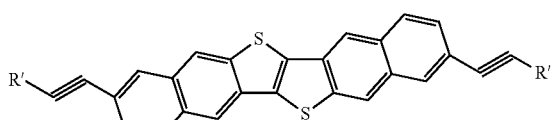
Formula (31)
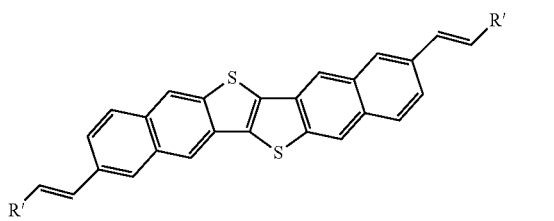
Formula (32)
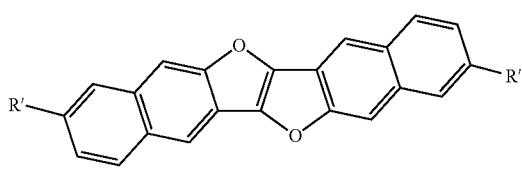
Formula (33)
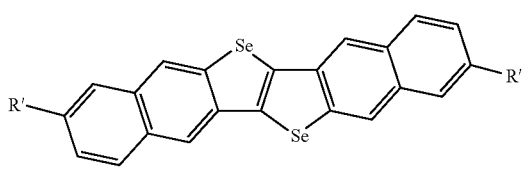
Formula (34)
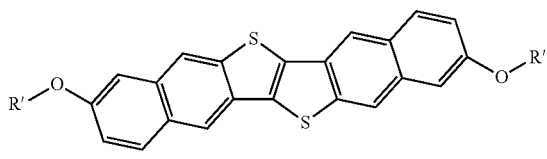
Formula (35)
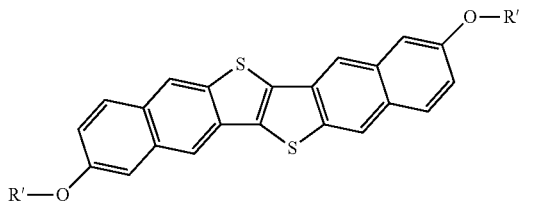
Formula (36)
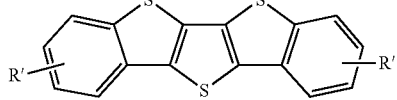
Formula (37)
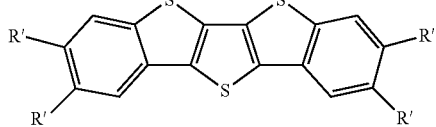
Formula (38)
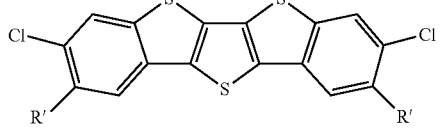
Formula (39)
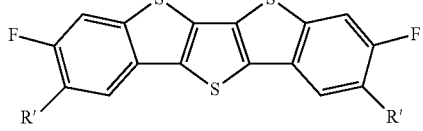
Formula (40)
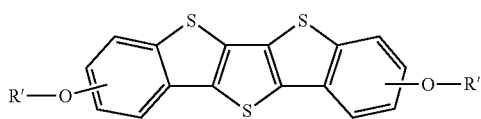
Formula (41)
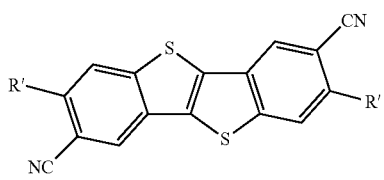
Formula (42)
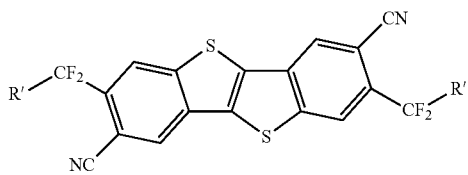
Formula (43)

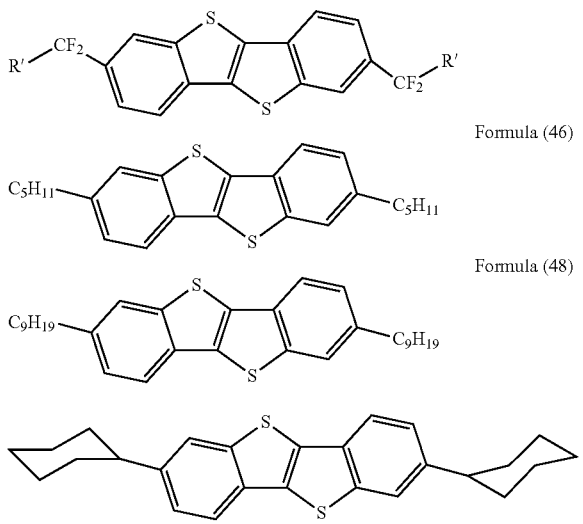
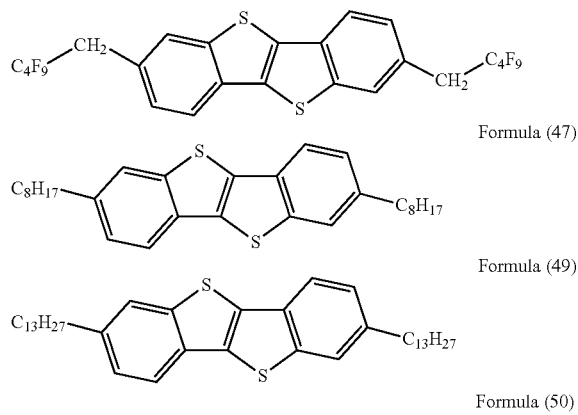

wherein each R' is independently alkyl or substituted alkyl containing from about 4 to about 20 carbon atoms, including from about 4 to about 16 carbon atoms.

The semiconducting compounds of Formulas (2), (3), (7), (8), (9), (13), (14), (15), (20), (21), and (43) through (50) are also exemplary compounds of Formula (II).

The semiconducting compounds of Formulas (2), (3), (13), (14), (15), (20), and (21) are also exemplary compounds of Formula (III).

The semiconducting compounds of Formulas (22), (23), (24), (25), (26), (27), (28), (29), (30), (31), (34), and (35) are also exemplary compounds of Formula (IV).

The semiconducting compounds of Formulas (36), (37), (38), (39), and (40) are also exemplary compounds of Formula (V).

The semiconducting compounds of Formulas (4), (5), (10), (11), (12), (18), (19), (24), (25), (26), (27), (37), (38), (39), (41), and (42) are also exemplary compounds of Formula (VI).

Various methods known in the arts can be used to make the small molecule semiconductors disclosed in this invention. For example, methods of producing the small molecule semiconductor of Formula (II) include reacting a 2,7-dihalo-BTBT A with an alkyne to form a 2,7-dialkyn-1-yl-BTBT 1. This initial reaction is illustrated below:

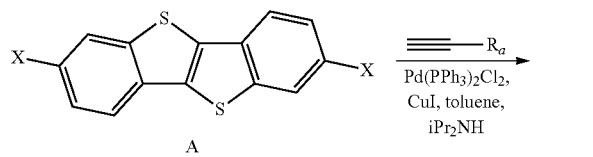

wherein X is a halogen, $R_a$ is alkyl, Ph(PPh$_3$)$_2$Cl$_2$ is bis(triphenylphosphine) palladium(II) chloride, CuI is copper iodide, and iPr$_2$NH is diisopropylamine. As shown here, the two $R_a$ groups are identical. However, the two $R_a$ groups can be different as well, for example by using a blocking/protecting group on one of the X groups, performing a first reaction with a first alkyne to convert the unprotected X group, removing the blocking/protecting group, then subsequently performing a second reaction with a second different alkyne.

Next, the 2,7-dialkyn-1-yl-BTBT 1 can be reduced to a 2,7-dialkyl-[1]benzothieno[3,2-b]benzothiophene 1a as depicted below:

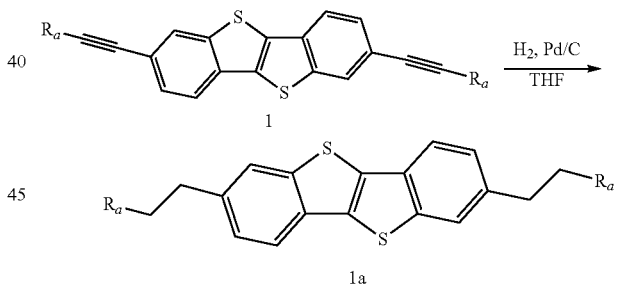

wherein Pd/C is a palladium on carbon catalyst and THF is tetrahydrofuran. Similar reactions can be performed for the other possible $R_a$ substituents.

Methods for preparing compounds 1a also includes the reaction of the [1]benzothieno[3,2-b]-benzothiophene core B with a substituted acid chloride in presence of aluminum trichloride to form a 2,7-diketonyl BTBT 2.

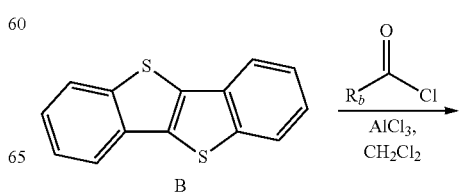

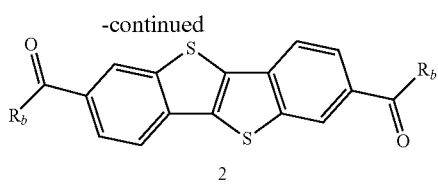

Next, the diketonyl BTBT 2 is deoxygenated using a modified Wolff-Kishner reduction using hydrazine in the presence of potassium hydroxide in diethylene glycol. This forms 2,7-dialkyl-[1]benzothieno[3,2-b]benzothiophene 1b.

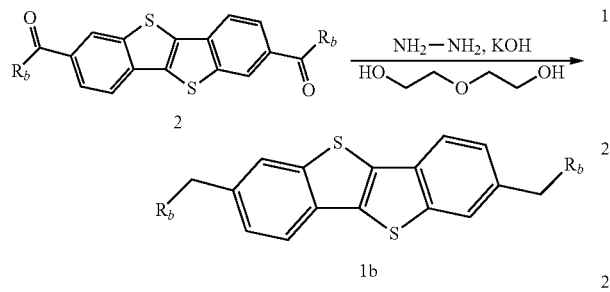

This 2-step method is particularly effective for short $R_b$ substituents ($C_2$-$C_8$).

The small molecule semiconductor by itself has poor film-forming properties, which is attributed to its crystalline or liquid crystalline nature. Thus, the semiconductor composition also comprises a polymer binder, which allows a uniform film to be achieved, significantly improving device performance. The polymer binder can be considered as forming a matrix within which the small molecule semiconductor is dispersed.

Any suitable polymer can be used as the polymer binder for the semiconductor composition. In some embodiments, the polymer is an amorphous polymer. The amorphous polymer may have a glass transition temperature less than the melting point temperature of the small molecule semiconductor. In other embodiments, the amorphous polymer has a glass transition temperature greater than the melting point temperature of the small molecule semiconductor. In embodiments, the polymer has a dielectric constant less than 4.5, preferably less than 3.5, including less than 3.0, as measured at 60 Hz at room temperature. In embodiments, the polymer is selected from polymers containing only C, H, F, Cl, or N atoms. In some embodiments, the polymer is a low polarity polymer, such as a hydrocarbon polymer or a fluorocarbon polymer without any polar groups. For example, polystyrene is an amorphous polymer and has a dielectric constant about 2.6. A list of other low polarity polymers includes but is not limited to the following: fluoropolyarylether, poly(p-xylylene), poly(vinyl toluene), poly(α-methyl styrene), poly(α-vinylnaphthalene), polyethylene, polypropylene, polyisoprene, poly(tetrafluoroethylene), poly(chlorotrifluoroethylene), poly(2-methyl-1,3-butadiene), poly(cyclohexyl methacrylate), poly(chlorostyrene), poly(4-methyl styrene), poly(vinyl, cyclohexane), polyphenylene, poly-p-phenylvinylidenes, poly(arylene ether), polyisobutylene, poly(2,6-dimethyl-1,4-phenylene ether), poly[1,1-(2-methyl propane)bis-(4-phenyl)carbonate], poly(a-a-a'-a' tetrafluoro-p-xylylene), fluorinated polyimide, poly(ethylene/tetrafluoroethylene), poly(ethylene/chlorotrifluoroethylene), fluorinated ethylene/propylene copolymer, poly(styrene-co-a-methyl styrene), poly(styrene/butadiene), poly(styrene/2,4-dimethylstyrene), CYTOP, poly(propylene-co-1-butene), poly(styrene-co-vinyl toluene), poly(styrene-block-butadiene-block-styrene), poly(styrene-block-isopene-block-styrene), terpene resin, poly(N-vinylcarbazole), polycarbazole, polytriarylamine, and the like.

It has been found that the mobility of the semiconducting layer formed by the semiconductor composition can be affected by the combination of small molecule semiconductor with certain polymers. The compounds of Formula (I) can be combined with many different polymers. In some particular embodiments, the polymer binder is a styrene-based polymer.

Styrene-based polymers contain a repeating unit derived from a styrene monomer of Formula (a):

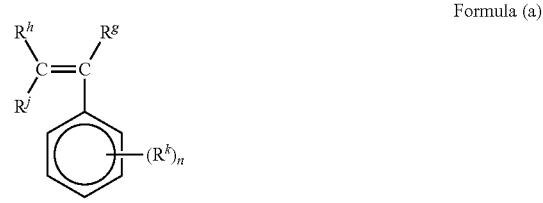

Formula (a)

wherein $R^g$, $R^h$, $R^j$, and $R^k$ are independently selected from hydrogen, halogen, and $C_1$-$C_{20}$ alkyl; and n is an integer from 0 to 5. The styrene monomer can be styrene ($R^g$, $R^h$, and $R^j$ are all hydrogen, n=0), alpha-methyl styrene ($R^g$ is methyl, $R^h$ and $R^j$ are hydrogen, n=0), or 4-methyl styrene ($R^g$, $R^h$, and $R^j$ are all hydrogen, n=1, $R^k$ is methyl in the 4-position). The term "styrene-based polymer" is intended to encompass both homopolymers and copolymers. The term "copolymer" is intended to encompass random, alternative, and block copolymers.

In other particular embodiments, the polymer binder is an arylamine-based polymer. An arylamine-based polymer has a repeating unit derived from a monomer having the structure of Formula (b), Formula (c) or Formula (d):

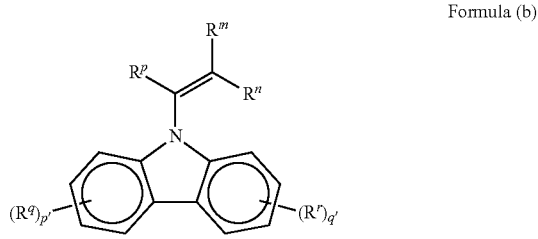

Formula (b)

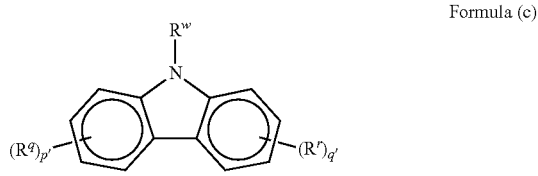

Formula (c)

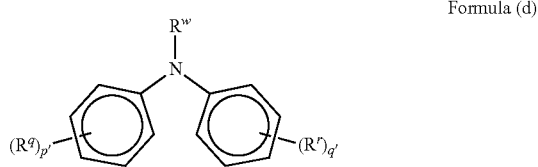

Formula (d)

wherein $R^m$, $R^n$, $R^p$, $R^q$, and $R^r$ are independently selected from hydrogen, halogen, $C_1$-$C_{20}$ alkyl, and aryl; p' and q' are independently an integer from 0 to 5; and $R^w$ is selected from $C_1$-$C_{20}$ alkyl, aryl, and substituted aryl. The term "arylamine-based" polymers is intended to encompass poly(N-vinyl carbazole), polycarbazole, and triarylamine-based polymers.

In specific embodiments, the styrene-based polymer and the arylamine-based polymer include polystyrene, poly(α-methyl styrene), poly(4-methyl styrene), poly(vinyl toluene), poly(α-methyl styrene-co-vinyl toluene), poly(styrene-block-butadiene-block-styrene), poly(styrene-block-isopene-block-styrene), a terpene resin, poly(styrene-co-2,4-dimethylstyrene), poly(chlorostyrene), poly(styrene-co-α-methyl styrene), poly(styrene/butadiene), poly(N-vinylcarbazole), polycarbazole, and polytriarylamines. It should be noted that one or more polymer binders can be used in the semiconductor composition.

The compound of Formula (II) works best when combined with the polymer binders discussed above, particularly, the styrene-based polymer or the arylamine-based polymer described above.

In more specific embodiments, the polymer binder is a styrene-based polymer. In particular embodiments, the styrene-based polymer has a weight average molecular weight of from about 40,000 to about 2,000,000. In some embodiments, the styrene-based polymer has a molecular weight of from about 100,000 to about 1,000,000. In one preferred embodiment, the polymer binder is polystyrene, poly(alpha-methyl styrene), or poly(4-methyl styrene) having a weight average molecular weight of from about 40,000 to about 2,000,000.

The compounds of Formulas (III), (IV), (V), and (VI) can generally be combined with any polymer binder. Exemplary polymer binders include the polymer binders discussed above, and other polymers such as poly(vinyl cinnamate), polysiloxanes, polypyrroles, polyacrylates, polymethacrylates, polyesters, and mixtures thereof. The polymers may have a weight average molecular weight of from about 10,000 to about 2,000,000, including from about 40,000 to about 1,000,000.

The weight ratio of the small molecule semiconductor of Formula (I) to the polymer binder may be from about 99:1 to about 1:3, including from about 10:1 to about 1:2, from about 5:1 to about 2:3, or from about 3:2 to about 3:4. In some embodiments, the weight ratio of the small molecule semiconductor of Formula (I) to the polymer binder is around 1:1. The weight ratio of the small molecule semiconductor of Formula (II) to the styrene-based polymer binder is desirably from about 3:2 to about 2:3, and works optimally at a ratio of about 1:1.

The semiconductor composition may further comprise a solvent in which the small molecule semiconductor and the polymer binder are soluble. Exemplary solvents used in the solution may include chlorinated solvents such as chlorobenzene, chlorotoluene, dichlorobenzene, dichloroethane, chloroform, trichlorobenzene, and the like; alcohols and diols such as propanol, butanol, hexanol, hexanediol, etc.; hydrocarbons or aromatic hydrocarbons such as hexane, heptane, toluene, decalin, xylene, ethyl benzene, tetrahydronaphthalene, methyl nanphthalene, mesitylene, trimethyl benzene, etc.; ketones such as acetone, methyl ethyl ketone, etc.; acetates, such as ethyl acetate; pyridine, tetrahydrofuran, and the like.

The small molecule semiconductor and the polymer binder are from about 0.05 to about 20 weight percent of the semiconductor composition, including from about 0.1 to about 10 weight percent of the semiconductor composition, or from about 0.1 to about 1.0 weight percent of the semiconductor composition.

In embodiments, the semiconductor composition comprising the small molecule semiconductor and the polymer binder may have a viscosity of from about 1.5 centipoise (cps) to about 100 cps, including from about 2 to about 20 cps. The use of a high molecular weight polymer binder will increase the viscosity of the semiconductor composition. As a result, it will help to form a uniform semiconductor layer upon using solution deposition techniques such as inkjet printing and spin coating.

Bottom-gate TFTs may be advantageous because they are generally simpler to fabricate. However, previous semiconductor/polymer composite systems have only achieved high mobility in top-gate devices. When the semiconductor composition of the present disclosure is utilized, high mobility can also be achieved in bottom-gate devices like those shown in FIGS. 1-3.

The semiconducting layer may be formed in an electronic device using conventional processes known in the art. In embodiments, the semiconducting layer is formed using solution depositing techniques. Exemplary solution depositing techniques include spin coating, blade coating, rod coating, dip coating, screen printing, ink jet printing, stamping, stencil printing, screen printing, gravure printing, flexography printing, and the like.

After being deposited, the semiconductor composition is dried and optionally annealed at a temperature below the melting point of the small molecular semiconductor compound to form the semiconducting layer. In some embodiments, in contrast to other small molecule semiconductor/polymer composite, there is absent of an annealing step during the fabrication of a semiconductor layer from the semiconductor composition. Annealing at a temperature higher than the melting point of the small molecule semiconductor would cause significant phase separation of the small molecule semiconductor and the polymer binder. As a result, the electronic device would show poor electrical performance. The semiconducting layer has a field effect mobility of at least 0.10 $cm^2/V\cdot sec$, or at least 0.15 $cm^2/V\cdot sec$, or at least 0.4 $cm^2/V\cdot sec$, including at least 0.5 $cm^2/V\cdot sec$.

The semiconducting layer formed using the semiconductor composition can be from about 5 nanometers to about 1000 nanometers deep, including from about 20 to about 100 nanometers in depth. In certain configurations, such as the configurations shown in FIGS. 1 and 4, the semiconducting layer completely covers the source and drain electrodes.

The performance of a TFT can be measured by mobility. The mobility is measured in units of $cm^2/V\cdot sec$; higher mobility is desired. The resulting TFT using the semiconductor composition of the present disclosure may have a field effect mobility of at least 0.1 $cm^2/V\cdot sec$. The TFT of the present disclosure may have a current on/off ratio of at least $10^5$, including at least $10^6$. The TFT comprising the semiconductor layer comprising the small molecule semiconductor of Formula (I) and a polymer binder has excellent stability in air. For example, upon exposure the ambient air, the field effect mobility may increase initially then leveled off. No decrease of field effect mobility over 2 weeks, including over 1 month.

A thin film transistor generally includes a substrate, an optional gate electrode, source electrode, drain electrode, and a dielectric layer in addition to the semiconducting layer.

The substrate may be composed of materials including but not limited to silicon, glass plate, plastic film or sheet. For structurally flexible devices, plastic substrate, such as for example polyester, polycarbonate, polyimide sheets and the like may be preferred. The thickness of the substrate may be from about 10 micrometers to over 10 millimeters with an exemplary thickness being from about 50 to about 100 micrometers, especially for a flexible plastic substrate and from about 0.5 to about 10 millimeters for a rigid substrate such as glass or silicon.

The dielectric layer generally can be an inorganic material film, an organic polymer film, or an organic-inorganic composite film. Examples of inorganic materials suitable as the dielectric layer include silicon oxide, silicon nitride, aluminum oxide, barium titanate, barium zirconium titanate and the like. Examples of suitable organic polymers include polyesters, polycarbonates, poly(vinyl phenol), polyimides, polystyrene, polymethacrylates, polyacrylates, epoxy resin and the like. The thickness of the dielectric layer depends on the dielectric constant of the material used and can be, for example, from about 10 nanometers to about 500 nanometers. The dielectric layer may have a conductivity that is, for example, less than about $10^{-12}$ Siemens per centimeter (S/cm). The dielectric layer is formed using conventional processes known in the art, including those processes described in forming the gate electrode.

In the present disclosure, the dielectric layer may be surface modified with a surface modifier. The semiconducting layer can be directly contacted with this modified dielectric layer surface. The contact may be complete or partial. This surface modification can also be considered as forming an interfacial layer between the dielectric layer and the semiconducting layer. In particular embodiments, the surface of the dielectric layer has been modified with an organosilane agent of Formula (A):

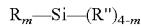

$$R_m\text{—Si—}(R'')_{4-m} \qquad \text{Formula (A)}$$

wherein R is hydrocarbon or fluorocarbon containing from 1 to about 20 carbon atoms, R" is halogen or alkoxy; and m is an integer from 1 to 4. Exemplary organosilanes include octyltrichlorosilane (OTS-8) (R=octyl, R"=chloro, m=1), dodecyltrichlorosilane, phenyltrichlorosilane, methyltrimethoxylsilane, phenylmethyldimethoxysilane, phenylmethyldichlorosilane, (3-phenylpropyl)dimethylchlorosilane, (3-phenyl propyl)methyldichlorosilane, phenyltrimethoxysilane, phenethyltrichlorosilane, and the like. In specific embodiments, the R comprises a phenyl group. Other surface modifiers such as polystyrene, polysiloxane, polysilsesquioxane can be used as well.

The gate electrode is composed of an electrically conductive material. It can be a thin metal film, a conducting polymer film, a conducting film made from conducting ink or paste, or the substrate itself, for example heavily doped silicon. Examples of gate electrode materials include but are not restricted to aluminum, gold, silver, chromium, indium tin oxide, conductive polymers such as polystyrene sulfonate-doped poly(3,4-ethylenedioxythiophene) (PSS-PEDOT), and conducting ink/paste comprised of carbon black/graphite. The gate electrode can be prepared by vacuum evaporation, sputtering of metals or conductive metal oxides, conventional lithography and etching, chemical vapor deposition, spin coating, casting or printing, or other deposition processes. The thickness of the gate electrode ranges for example from about 10 to about 200 nanometers for metal films and from about 1 to about 10 micrometers for conductive polymers. Typical materials suitable for use as source and drain electrodes include those of the gate electrode materials such as aluminum, gold, silver, chromium, zinc, indium, conductive metal oxides such as zinc-gallium oxide, indium tin oxide, indium-antimony oxide, conducting polymers and conducting inks. Typical thicknesses of source and drain electrodes are, for example, from about 40 nanometers to about 1 micrometer, including more specific thicknesses of from about 100 to about 400 nanometers.

Typical materials suitable for use as source and drain electrodes include those of the gate electrode materials such as gold, silver, nickel, aluminum, platinum, conducting polymers, and conducting inks. In specific embodiments, the electrode materials provide low contact resistance to the semiconductor. Typical thicknesses are about, for example, from about 40 nanometers to about 1 micrometer with a more specific thickness being about 100 to about 400 nanometers. The OTFT devices of the present disclosure contain a semiconductor channel. The semiconductor channel width may be, for example, from about 5 micrometers to about 5 millimeters with a specific channel width being about 100 micrometers to about 1 millimeter. The semiconductor channel length may be, for example, from about 1 micrometer to about 1 millimeter with a more specific channel length being from about 5 micrometers to about 100 micrometers.

The source electrode is grounded and a bias voltage of, for example, about 0 volt to about 80 volts is applied to the drain electrode to collect the charge carriers transported across the semiconductor channel when a voltage of, for example, about +10 volts to about −80 volts is applied to the gate electrode. The electrodes may be formed or deposited using conventional processes known in the art.

If desired, a barrier layer may also be deposited on top of the TFT to protect it from environmental conditions, such as light, oxygen and moisture, etc. which can degrade its electrical properties. Such barrier layers are known in the art and may simply consist of polymers.

The various components of the OTFT may be deposited upon the substrate in any order. Generally, however, the gate electrode and the semiconducting layer should both be in contact with the gate dielectric layer. In addition, the source and drain electrodes should both be in contact with the semiconducting layer. The phrase "in any order" includes sequential and simultaneous formation. For example, the source electrode and the drain electrode can be formed simultaneously or sequentially. The term "on" or "upon" the substrate refers to the various layers and components with reference to the substrate as being the bottom or support for the layers and components which are on top of it. In other words, all of the components are on the substrate, even though they do not all directly contact the substrate. For example, both the dielectric layer and the semiconductor layer are on the substrate, even though one layer is closer to the substrate than the other layer. The resulting TFT has good mobility and good current on/off ratio.

The following examples are for purposes of further illustrating the present disclosure. The examples are merely illustrative and are not intended to limit devices made in accordance with the disclosure to the materials, conditions, or process parameters set forth therein. All parts are percentages by volume unless otherwise indicated.

EXAMPLES

Synthesis of Small Molecule Semiconductor 2,7-ditridecyl-[1]benzothieno[3,2-b]benzothiophene (2,7-ditridecyl-BTBT) (Formula (49)) was produced as follows.

A 50 mL Schlenk flask was charged with 2,7-diiodo-BTBT (0.51 grams, 1.036 mmol) and tridec-1-yne (0.934 grams, 5.18 mmol). Toluene (15 ml) and diisopropylamine (15 ml) were added and the reaction was degassed with two freeze/pump/thaw cycles. To the frozen reaction mixture was added bis(triphenylphosphine)palladium(II) chloride (0.145 grams, 0.207 mmol) and copper(I) iodide (0.079 grams, 0.415 mmol). The reaction was subjected to a final freeze/pump/ thaw cycle and stirred under argon. After 18 hours the reaction was filtered and the filtrate was concentrated to dryness using a rotary evaporator. The crude product was purified using a Biotage SP1 chromatography system (50 grams SNAP, 0-20% CH$_2$Cl$_2$ in hexanes). The product, 2,7-ditridecyn-1-yl-BTBT, was isolated and recrystallized from hexanes. The structure was confirmed by $^1$H and $^{13}$C NMR spectroscopy. A yield of 0.25 g (40%) was realized. This step is illustrated below:

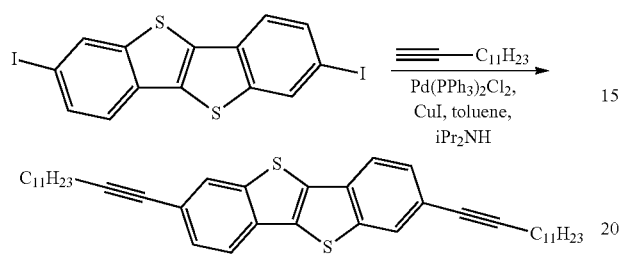

Next, in a 250 mL round-bottomed flask a solution of 2,7-ditridecyn-1-yl-BTBT (0.47 grams, 0.787 mmol) in tetrahydrofuran (50 ml) was treated with Pd/C (0.5 grams, 4.70 mmol). The flask was carefully evacuated under vacuum and purged with H$_2$ gas three times. The reaction was stirred under an H$_2$ atmosphere (balloon) until no starting material was detected by TLC. After 18 hours the reaction was concentrated on a rotary evaporator, resuspended in hexane and filtered through a short silica plug (hexanes). The product was practically pure by TLC and was recrystallized from hexanes. The structure was confirmed by $^1$H and $^{13}$C NMR spectroscopy. A yield of 0.40 g (84%) was realized to obtain the final product. This step is illustrated below:

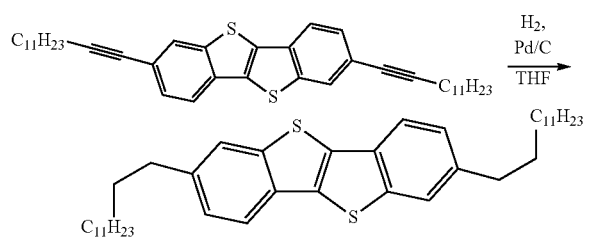

Synthesis of Small Molecule Semiconductor 2,7-dipentyl-[1]benzothieno[3,2-b]benzothiophene was produced (2,7-dipentyl-BTBT) (Formula (46)).

In a 250 mL 3-neck round-bottomed flask benzo[b]benzo[4,5]thieno[2,3-d]thiophene (1 grams, 4.16 mmol) was dissolved in CH$_2$Cl$_2$ (100 ml) and cooled to minus 10° C. The reaction was treated with AlCl$_3$ (3.05 grams, 22.88 mmol) and the resulting brown suspension was cooled to −78° C. The reaction was treated dropwise with pentanoyl chloride (2.52 ml, 20.80 mmol) and the resulting red suspension was stirred at this temperature under an Argon atmosphere. After 1 hour, the cooling bath was removed and the reaction was warmed to room temperature and stirred under an Argon atmosphere. After 48 hours the reaction was poured over ice and was stirred for 1 hour. The crude product was collected by vacuum filtration and washed sequentially with water (50 mL) and methanol (50 mL). The crude product was purified by recrystallization from toluene. The structure was confirmed by $^1$H and $^{13}$C NMR spectroscopy. A yield of 0.65 g (38%) was realized.

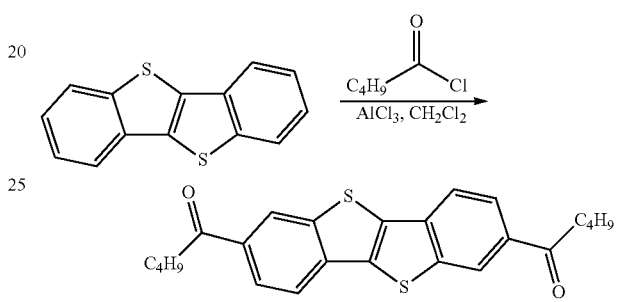

In a 250 mL 3-necked round-bottomed flask potassium hydroxide (0.453 g, 8.08 mmol) was dissolved in diethylene glycol (70 ml). The reaction was treated with 1,1'-(benzo[b]benzo[4,5]thieno[2,3-d]thiophene-2,7-diyl)bis(pentan-1-one) (0.600 g, 1.469 mmol) and hydrazine monohydrate (1.817 ml, 37.4 mmol) and the resulting suspension was heated to 100° C. After 1 hour the reaction was heated to 210° C. After 5 hours the heating source was removed and the reaction was cooled to room temperature and stirred overnight. The crude product was collected by vacuum filtration, then washed with water (50 mL) and methanol (50 mL). The product was purified by column chromatography on silica gel eluting with hexane and then recrystallized from hexane. The structure was confirmed by $^1$H and $^{13}$C NMR spectroscopy. A yield of 0.25 g (45%) was realized to obtain the final product.

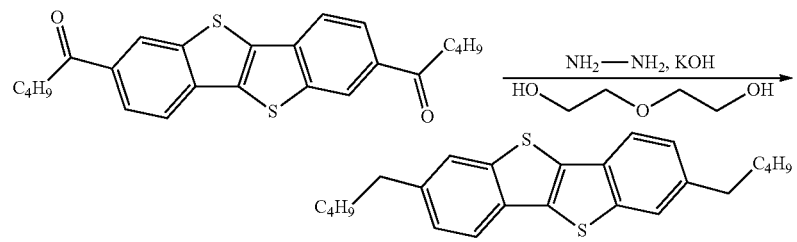

Comparative Examples 1-3

The three Comparative Examples were generally prepared as follows. An n-doped silicon wafer with 200-nm thermally grown silicon oxide dielectric layer was used as substrate. A 0.6 wt % semiconductor solution of 2,7-ditridecyl-BTBT in chlorobenzene was spin coated on the dielectric layer. After drying at 70-80° C. for 30 minutes, gold source and drain electrodes were vacuum evaporated on top of the semiconducting layer to complete the devices (see FIG. 3). The devices were characterized with Keithley 4200 SCS and ambient conditions. At least 10 transistors were fabricated and characterized for each Example. The morphology of the semiconducting layer was examined by optical microscopy.

In Comparative Example 1, the surface of the silicon oxide dielectric layer was not modified.

In Comparative Example 2, the surface of the silicon oxide dielectric layer was modified with HMDS prior to deposition of the semiconductor solution.

In Comparative Example 3, the surface of the silicon oxide dielectric layer was modified with OTS-8 prior to deposition of the semiconductor solution.

Comparative Examples 4-6

3 milligrams of 2,7-BTBT were dissolved in 1 gram dichlorobenzene solvent along with 3 milligrams of poly(3,3'''-didodecylquaterthiophene), a polymer also known as PQT-12 and having the structure shown below:

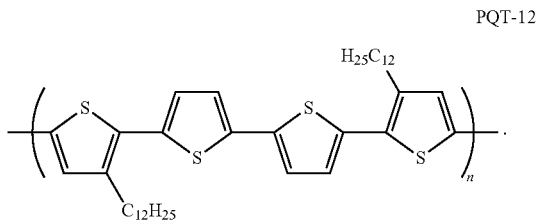

PQT-12

The semiconductor solution was spin coated onto an OTS-8 modified substrate to form a uniform film. After being dried at 70-80° C. for 30 minutes, gold source and drain electrodes were vacuum evaporated on top of the semiconducting layer to complete the devices. At least 10 transistors were fabricated and characterized for each Example.

In Comparative Example 4, the devices were not subsequently annealed after deposition of the source and drain electrodes.

In Comparative Example 5, the devices were subsequently annealed at a temperature of 130° C. for 10 minutes in a vacuum oven.

In Comparative Example 6, the devices were subsequently annealed at a temperature of 140° C. for 10 minutes in a vacuum oven Examples 1 Through 9

15 mg polystyrene and 15 mg 2,7-ditridecyl-BTBT were dissolved in 2 grams chlorobenzene solvent. The semiconductor solution was spin coated onto an OTS-8 modified substrate to form a uniform film. After being dried at 70-80° C. for 30 minutes, gold source and drain electrodes were vacuum evaporated on top of the semiconducting layer to complete the devices. At least 10 transistors were fabricated and characterized for each Example.

In Example 1, the polystyrene had a molecular weight of about 45,000.

In Example 2, the polystyrene had a molecular weight of about 280,000.

In Example 3, poly(alpha-methylstyrene) having a molecular weight of 100,000 was used instead of polystyrene.

In Example 4, poly(4-methylstryrene) having a molecular weight of 72,000 was used instead of polystyrene. Also, phenyltrichlorosilane (PTS) was used instead of OTS-8.

In Example 5, a copolymer, poly(vinyl toluene-co-alpha-methyl styrene) (melt viscosity, 100 poise at 161° C.), was used instead of polystyrene. Also, PTS was used instead of OTS-8.

In Example 6, poly(N-vinyl carbazole) with a molecular weight of 1,100,000 was used instead of polystyrene. Also, PTS was used instead of OTS-8.

In Example 7, polystyrene was used for the polymer and hexamethyldisilazane (HMDS) was used instead of OTS-8. 2,7-dipentyl-BTBT was used instead of 2,7-ditridecyl-BTBT.

In Example 8, polystyrene was used for the polymer and PTS was used instead of OTS-8. 2,7-dipentyl-BTBT was used instead of 2,7-ditridecyl-BTBT.

In Example 9, poly(alpha-methyl styrene) was used for the polymer and PTS was used instead of OTS-8. 2,7-dipentyl-BTBT was used instead of 2,7-ditridecyl-BTBT.

Comparative Example 7

The transistor device made in Example 2 was thermally annealed at 130° C. for 5 minutes. After cooling down to room temperature, the mobility was measured again.

Results

Table 1 summarizes the performance of the transistors of Comparative Examples 1-7 and Examples 1-9.

TABLE 1

| | | | | Mobility | | |
| Example | Surface Modified | $M_w$ of polymer | Film Uniformity | Lowest Mobility ($cm^2/V \cdot sec$) | Average Mobility ($cm^2/V \cdot sec$) | Highest Mobility ($cm^2/V \cdot sec$) |
| --- | --- | --- | --- | --- | --- | --- |
| CE1 | None | N/A | Uniform | 0.0001 | 0.01 | 0.05 |
| CE2 | HMDS | N/A | Not uniform | 0.02 | 0.08 | 0.47 |
| CE3 | OTS-8 | N/A | No film | — | — | — |
| CE4 | OTS-8 | N/A | Uniform | 0.02 | 0.005 | 0.01 |
| CE5 | OTS-8 | N/A | Uniform | 0.05 | 0.02 | 0.04 |
| CE6 | OTS-8 | N/A | Uniform | 0.09 | 0.04 | 0.06 |
| E1 | OTS-8 | 45,000 | Uniform, partial coverage | 0.01 | 0.19 | 0.46 |
| E2 | OTS-8 | 280,000 | Uniform | 0.29 | 0.48 | 0.77 |

TABLE 1-continued

Mobility

| Example | Surface Modified | $M_w$ of polymer | Film Uniformity | Lowest Mobility ($cm^2/V \cdot sec$) | Average Mobility ($cm^2/V \cdot sec$) | Highest Mobility ($cm^2/V \cdot sec$) |
|---|---|---|---|---|---|---|
| E3 | OTS-8 | 100,000 | Uniform | 0.3 | 0.52 | 0.81 |
| E4 | PTS | 72,000 | Uniform | 0.25 | 0.34 | 0.56 |
| E5 | PTS | N/A | Uniform | 0.28 | 0.45 | 0.78 |
| E6 | PTS | 1,100,000 | Uniform | 0.1 | 0.2 | 0.3 |
| E7 | HMDS | 280,000 | Uniform | 0.5 | 1.0 | 2.0 |
| E8 | PTS | 280,000 | Uniform | 1.2 | 2.5 | 2.9 |
| E9 | PTS | 300,000 | Uniform | 1.3 | 2.6 | 3.0 |
| CE7 | OTS-8 | 280,000 | Obvious phase separation after annealing | 0.00002 | 0.00015 | 0.002 |

A relatively uniform film was obtained in Comparative Example 1 on an unmodified substrate. However, the devices exhibited very low field-effect mobility.

In the devices with an HMDS-modified surface of Comparative Example 2, mobility of up to almost 0.5 $cm^2/V \cdot sec$ was observed. However, mobility as low as 0.02 $cm^2/V \cdot sec$ was also observed. The variation of the mobility of these devices was more than one order of magnitude, possibly because of the lack of uniformity of the film.

A film could not be coated onto the OTS-8-modified substrates of Comparative Example 3. The low viscosity of the semiconductor composition may have been the cause.

Figure 5A:
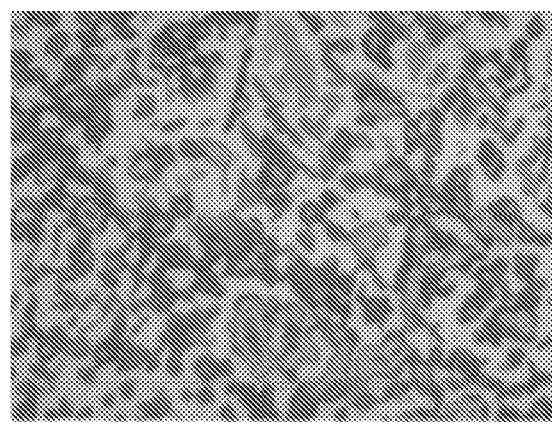
FIG. 5A is a first photomicrograph of a 2,7-tridecyl-[1]benzothieno[3,2-b]benzothiophene layer on an HMDS-modified SiO₂ surface, showing a majority area.
Figure 5B:
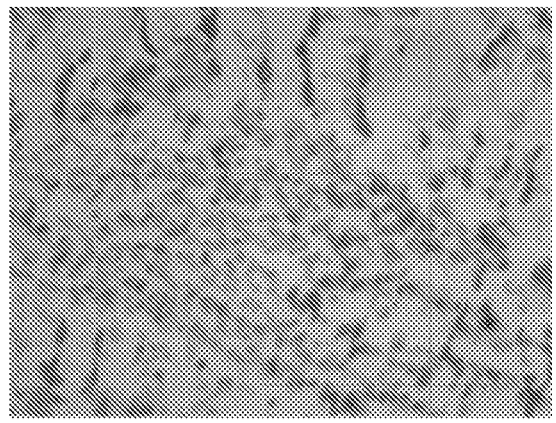
FIG. 5B is a second photomicrograph of a 2,7-tridecyl-[1]benzothieno[3,2-b]benzothiophene layer on an HMDS-modified SiO₂ surface, showing another majority area.
Figure 5C:
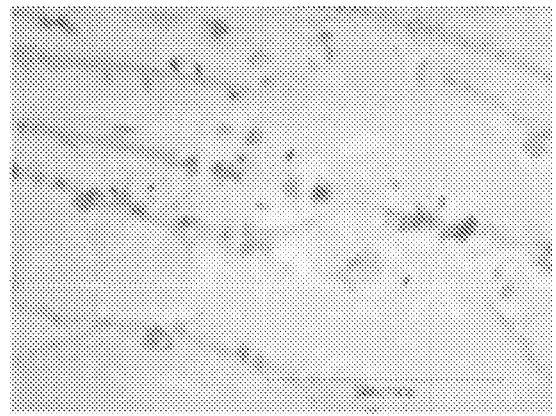
FIG. 5C is a third photomicrograph of a 2,7-tridecyl-[1]benzothieno[3,2-b]benzothiophene layer on an HMDS-modified SiO₂ surface, showing a minority area.

FIGS. 5A-5C are three photomicrographs showing three typical morphologies found in the thin films of Comparative Example 2. FIG. 5A and FIG. 5B show a majority area of the semiconductor layer, which offered the low mobility. FIG. 5C shows a minority area that offered the highest mobility. Both FIG. 5A and FIG. 5B showed small domains and non-uniform coating as revealed by the different shades, while FIG. 5C showed a large domain with a uniform layer.

In Comparative Examples 4-6, the semiconducting layer included 2,7-ditridecyl-BTBT and PQT-12. The mobility of these layers was not very high, and were comparable to semiconducting layers made of pure polythiophene when annealed. Put another way, the presence of 2,7-ditridecyl-BTBT did not improve the mobility of the semiconducting layer at all, as might have been expected. These results suggest that not all polymers are suitable for use as the polymer binder of the present disclosure, particularly for bottom-gate devices.

The semiconducting layers of Examples 1 to 9 offered better film uniformity and better performance. Higher average mobility was achieved, particularly when the styrene-based polymer or the arylamine-based polymer (e.g. poly(N-vinyl carbazole)) with the higher molecular weight was used. The highest mobility was up to 0.81 $cm^2/V \cdot sec$ for a composite semiconductor of polymer binder and 2,7-ditridecyl-[1]benzothieno[3,2-b]benzothiophene, and up to 3.0 $cm^2/V \cdot s$ for the composite semiconductor of 2,7-dipentyl-[1]benzothieno[3,2-b]benzothiophene in polymer binder, and the variation in mobility was greatly reduced. Preferably, no annealing step is used. As shown in Comparative Example 7, the annealed device showed significantly lower mobility.

Figure 6:
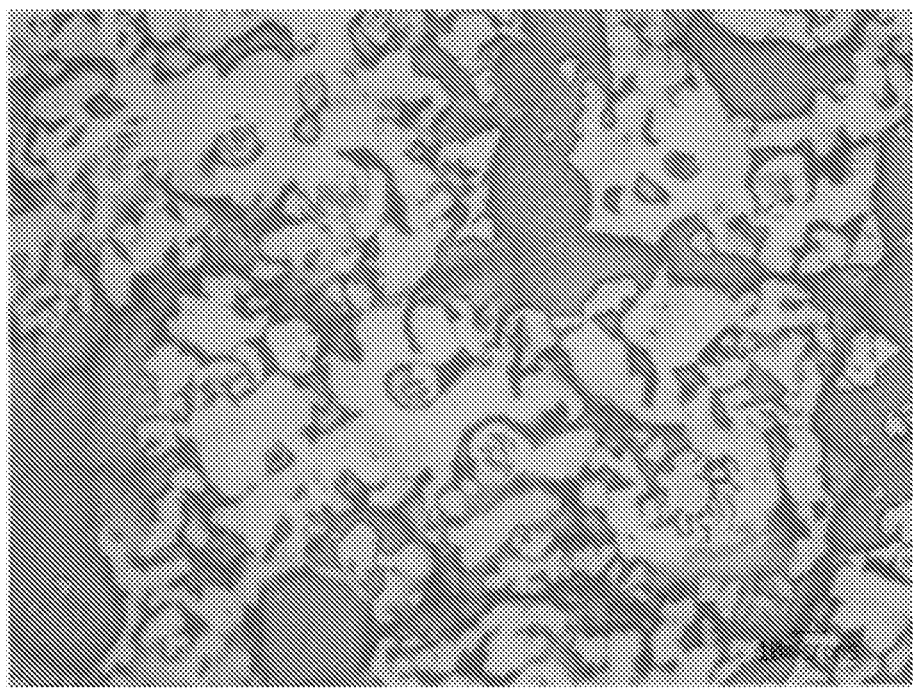
FIG. 6 is a photomicrograph of a thin film comprising polystyrene and 2,7-tridecyl-[1]benzothieno[3,2-b]benzothiophene on an OTS-8-modified SiO₂ surface.

FIG. 6 is a photomicrograph showing the morphology of a thin film containing 2,7-ditridecyl-BTBT and polystyrene. The composition exhibited large phase separated domains or polymer dispersed liquid crystalline domains, seen here as the lighter yellow shade. The domain size was as large as 100 μm in length, in contrast to the small domains shown in FIG. 5A. Without being limited by theory, it appears that this morphology enables high field-effect mobility.

Figure 7:
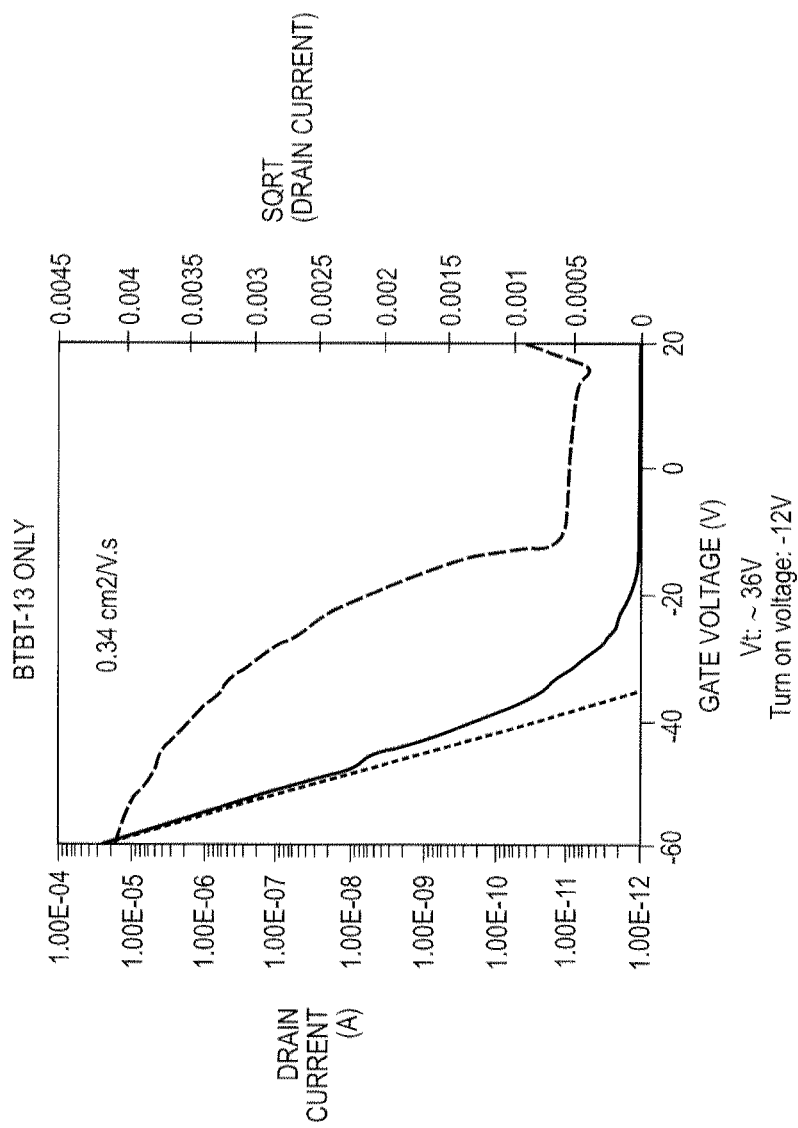
FIG. 7 is a graph showing the I-V curve of a TFT with a semiconducting layer of 2,7-tridecyl-[1]benzothieno[3,2-b]benzothiophene.
Figure 8:
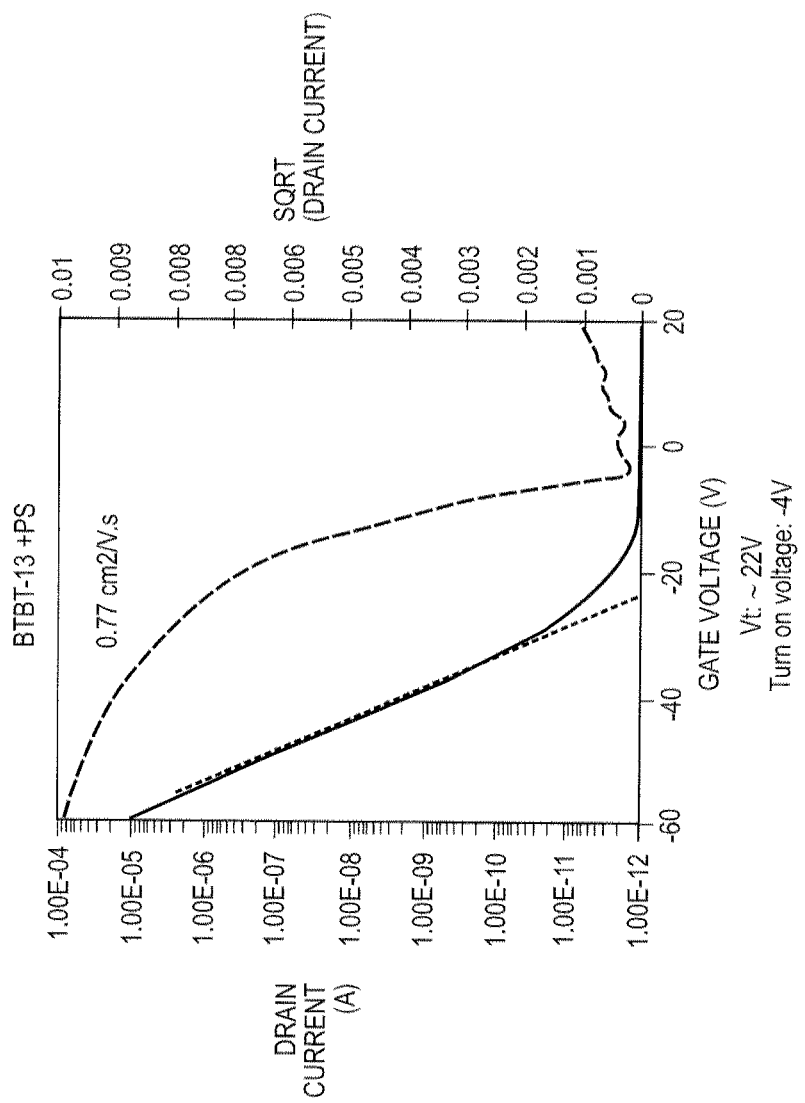
FIG. 8 is a graph showing the I-V curve of a TFT with a semiconducting layer of 2,7-tridecyl-[1]benzothieno[3,2-b]benzothiophene and polystyrene.

The use of a styrene-based polymer as the polymer binder improved not only the mobility, but also other device characteristics. FIG. 7 is a graph showing the I-V curve for a TFT with a semiconducting layer consisting only of 2,7-ditridecyl-BTBT. FIG. 8 shows the I-V curve for a TFT including a semiconducting layer containing 2,7-ditridecyl-BTBT and polystyrene. These devices had a channel length of 90 micrometers and a channel width of 1,000 micrometers. In both figures, the curved dotted line is the drain current, while the solid line is the square root of the drain current. The straight dotted line is a best fit for the square root of the drain current.

The device of FIG. 7 exhibited a large turn-on voltage of around −12 V and a large threshold voltage of about −36 V. In contrast, the device of FIG. 8 showed a turn-on voltage of close to zero, and had a much smaller threshold voltage of around −22 V. The device of FIG. 7 achieved a mobility of 0.34 $cm^2/V \cdot sec$, while the device of FIG. 8 achieved a mobility of 0.77 $cm^2/V \cdot sec$. These I-V curves show that the addition of a polystyrene binder improved turn-on voltages and threshold voltage in addition to the beneficial mobility effects.

The devices of Examples 1 to 9 exhibited excellent stability. When fabricated and characterized in open-air, a high current on/off ratio of up to $10^7$ with an extremely low off current ($10^{-12}$ amps) were achieved. No increase of the off current and no reduction of the mobility were observed upon exposure of the devices to ambient air for more than one week.

These compositions are more compatible with roll-to-roll manufacturing since annealing is not required. The compositions of the Examples also showed high field-effect mobility in TFTs with a bottom-gate device configuration. In contrast, previous semiconductor/polymer compositions only achieved high mobility in top-gate TFTs. A bottom-gate TFT configuration enables fabrication simplicity.

It will be appreciated that variants of the above-disclosed and other features and functions, or alternatives thereof, may be combined into many other different systems or applications. Various presently unforeseen or unanticipated alternatives, modifications, variations or improvements therein may be subsequently made by those skilled in the art which are also intended to be encompassed by the following claims.

The invention claimed is:
1. A semiconductor composition comprising:
a polymer binder; and
a small molecule semiconductor of Formula (I):

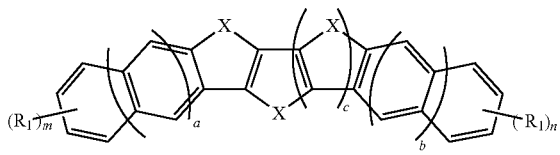

Formula (I)

wherein each $R_1$ is independently selected from alkyl, substituted alkyl, alkenyl, substituted alkenyl, alkynyl, substituted alkynyl, aryl, substituted aryl, heteroaryl, substituted heteroaryl, alkoxy, alkylthio, trialkylsilyl, ketonyl, cyano, and halogen; m and n are the number of R1 sidechains on their respective phenyl or naphthyl ring, and are independently an integer from 0 to 6; X is selected from the group consisting of O, S, and Se; and a, b, and c are independently 0 or 1;
wherein the semiconductor composition is capable of forming a layer having a field-effect mobility greater than 0.10 cm$^2$/V·sec.

2. The semiconductor composition of claim 1, wherein the small molecule semiconductor has the structure of Formula (II):

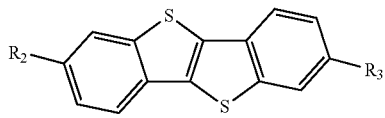

Formula (II)

wherein $R_2$ and $R_3$ are independently selected from alkenyl, substituted alkenyl, alkynyl, substituted alkynyl, aryl, substituted aryl, heteroaryl, substituted heteroaryl, alkoxy, alkylthio, trialkylsilyl, ketonyl, cyano, and halogen.

3. The semiconductor composition of claim 2, wherein the polymer binder is a styrene-based polymer or an arylamine-based polymer.

4. The semiconductor composition of claim 3, wherein the polymer binder is polystyrene, poly(α-methyl styrene), poly(4-methyl styrene), poly(alpha-methyl styreneco-vinyl toluene), poly(styrene-block-butadiene-block-styrene), poly(styrene-block-isopene-block-styrene), poly (vinyl toluene), a terpene resin, poly(styrene-co-2,4-dimethylstyrene), poly (chlorostyrene), poly(styrene-co-α-methyl styrene), poly(styreneco-butadiene), polycarbazole, a polytriarylamine, or poly(N-vinylcarbazole).

5. The semiconductor composition of claim 2, wherein the polymer binder is a styrene-based polymer having a weight average molecular weight of from about 40,000 to about 2,000,000.

6. The semiconductor composition of claim 1, wherein the polymer binder has a dielectric constant less than 3.5.

7. The semiconductor composition of claim 1, wherein the small molecule semiconductor has the structure of Formula (II):

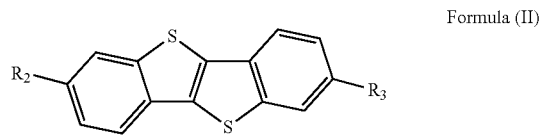

Formula (II)

wherein $R_2$, and $R_3$ are independently alkyl or substituted alkyl; and wherein the polymer binder is a styrene-based polymer or an arylamine-based polymer.

8. The semiconductor composition of claim 7, wherein the polymer binder is polystyrene, poly(α-methyl styrene), poly(4-methyl styrene), poly(alpha-methyl styreneco-vinyl toluene), poly(styrene-block-butadiene-block-styrene), poly(styrene-block-isopene-block-styrene), poly (vinyl toluene), a terpene resin, poly(styrene-co-2,4-dimethylstyrene), poly (chlorostyrene), poly(styrene-co-α-methyl styrene), poly(styreneco-butadiene), polycarbazole, a polytriarylamine, or poly(N-vinylcarbazole).

9. The semiconductor composition of claim 8, wherein the polymer binder is a styrene-based polymer having a weight average molecular weight of from about 100,000 to about 1,000,000.

10. The semiconductor composition of claim 1, wherein the small molecule semiconductor has the structure of Formula (III):

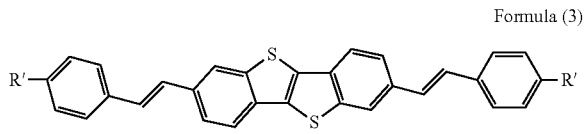

Formula (3)

wherein $R_8$, and $R_9$ are independently alkyl or substituted alkyl; and each Ar is independently an arylene or heteroarylene group.

11. The semiconductor composition of claim 1, wherein the small molecule semiconductor is selected from Formulas (1) through (50):

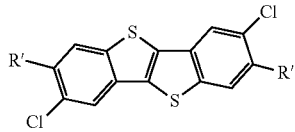

Formula (1)

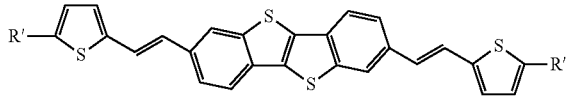

Formula (2)

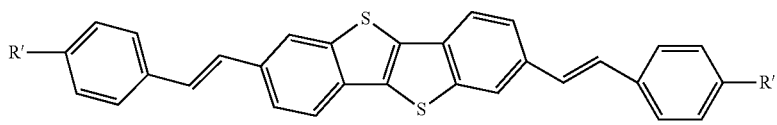

Formula (3)

-continued
Formula (4)
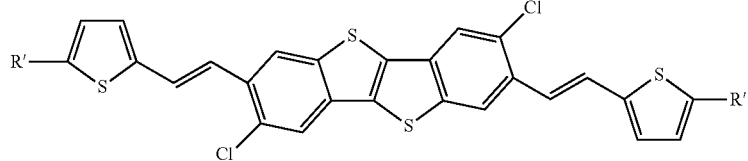
Formula (5)
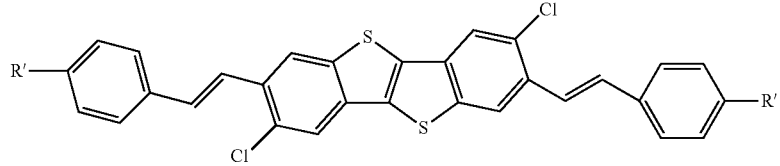
Formula (6)
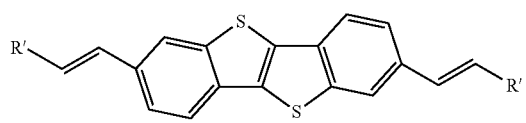
Formula (7)
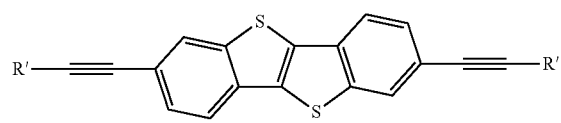
Formula (8)
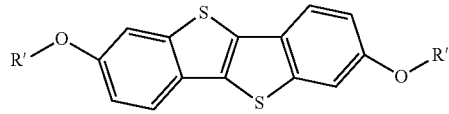
Formula (9)
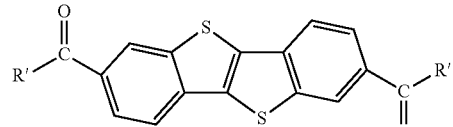
Formula (10)
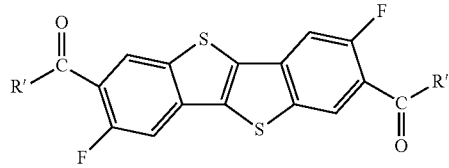
Formula (11)
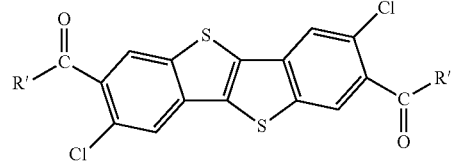
Formula (12)
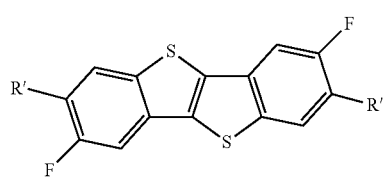
Formula (13)
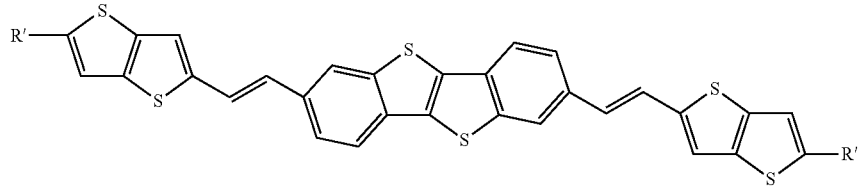
Formula (14)
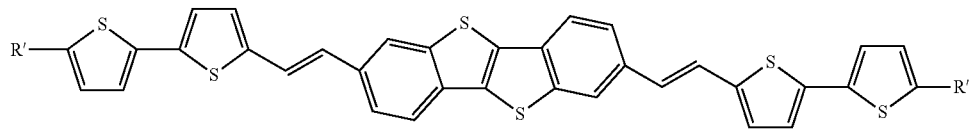
Formula (15)
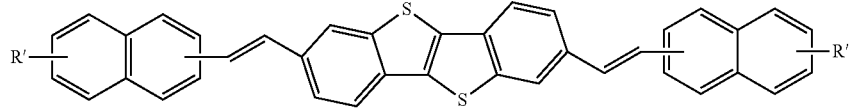
Formula (16)
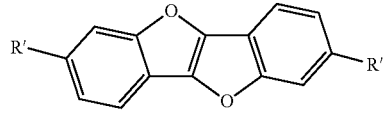
Formula (17)
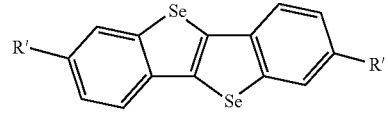

-continued
Formula (18)
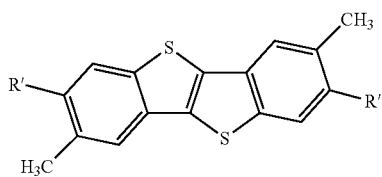
Formula (19)
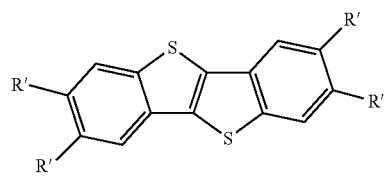
Formula (20)
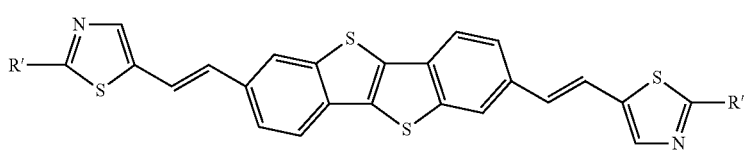
Formula (21)
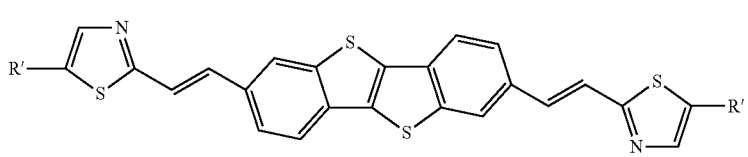
Formula (22)
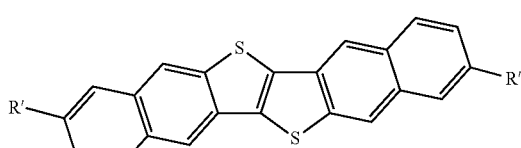
Formula (23)
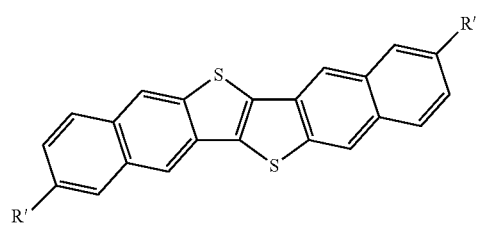
Formula (24)
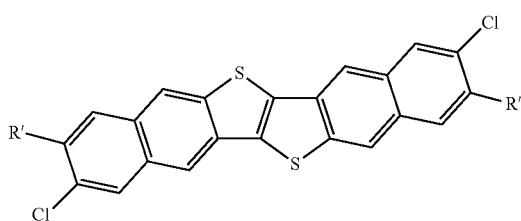
Formula (25)
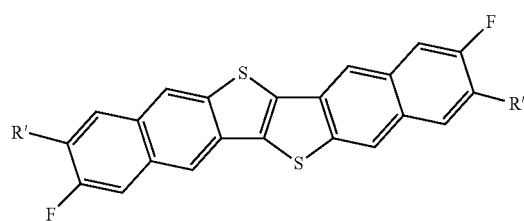
Formula (26)
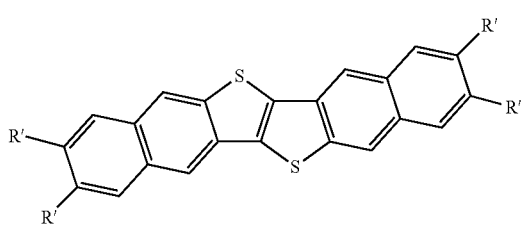
Formula (27)
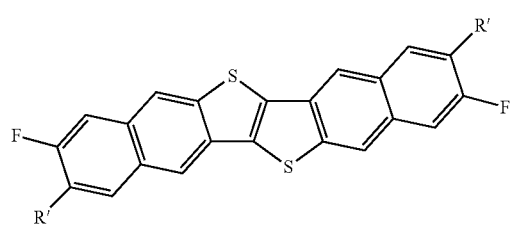
Formula (28)
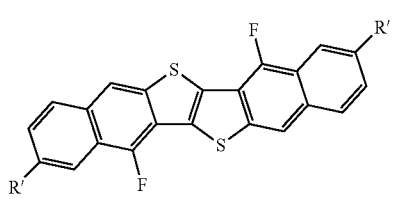
Formula (29)
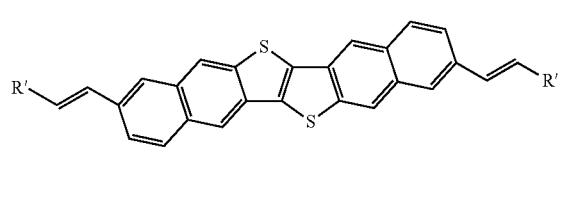

-continued
Formula (30)
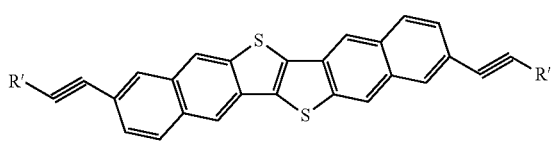
Formula (31)
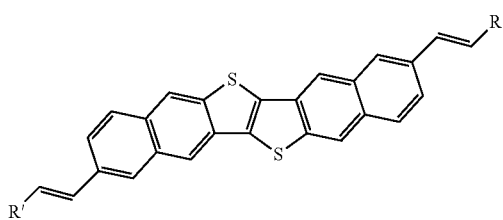
Formula (32)
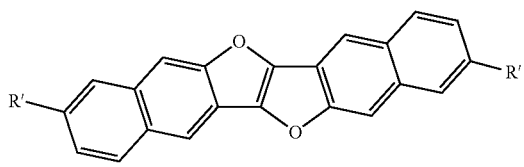
Formula (33)
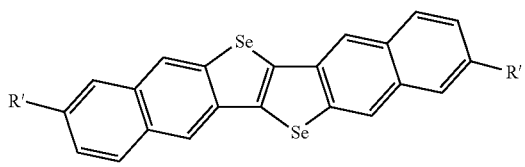
Formula (34)
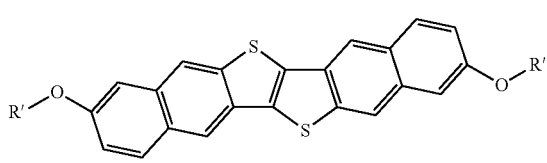
Formula (35)
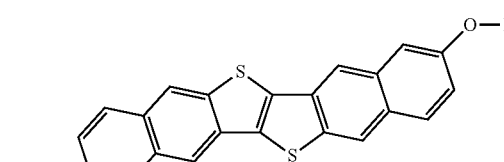
Formula (36)
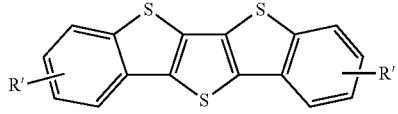
Formula (37)
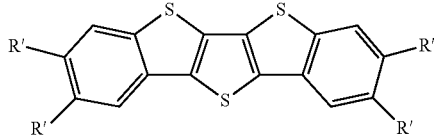
Formula (38)
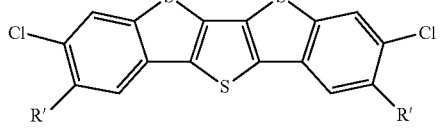
Formula (39)
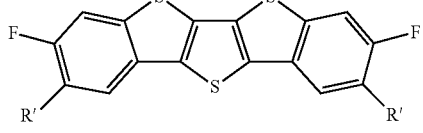
Formula (40)
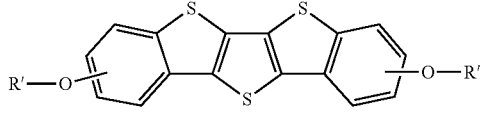
Formula (41)
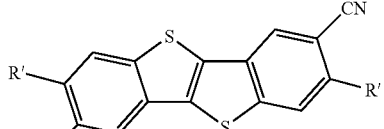
Formula (42)
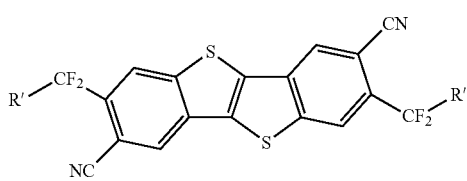
Formula (43)
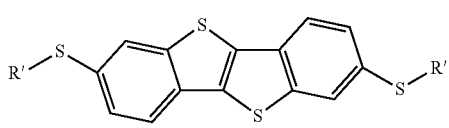
Formula (44)
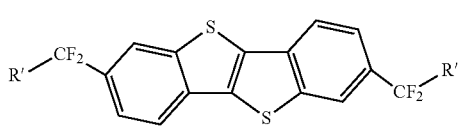
Formula (45)
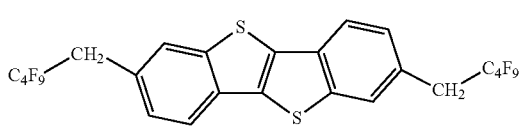
Formula (46)
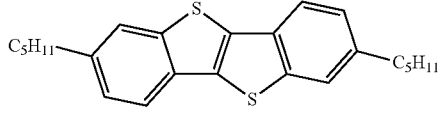
Formula (47)
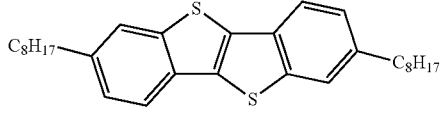

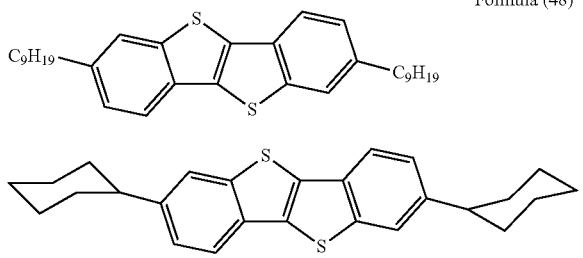

Formula (48)

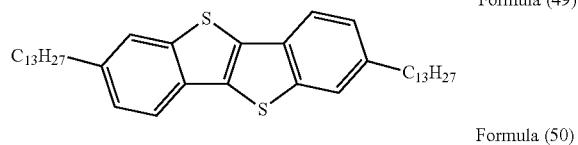

Formula (49)

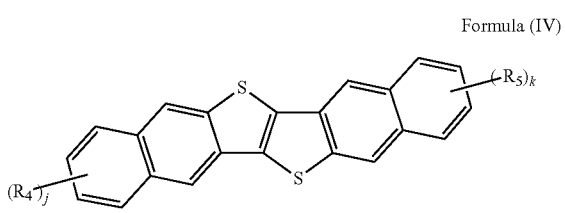

Formula (50)

wherein each R' is independently alkyl or substituted alkyl containing from about 4 to about 20 carbon atoms.

12. The semiconductor composition of claim 1, wherein the small molecule semiconductor has the structure of Formula (IV):

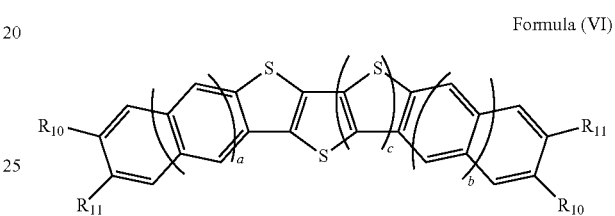

Formula (IV)

wherein $R_4$ and $R_5$ are independently selected from alkyl, substituted alkyl, alkenyl, substituted alkenyl, alkynyl, substituted alkynyl, aryl, substituted aryl, heteroaryl, substituted heteroaryl, alkoxy, alkylthio, trialkylsilyl, ketonyl, cyano, and halogen; and j and k are independently an integer from 0 to 6.

13. The semiconductor composition of claim 12, wherein $R_4$ and $R_5$ are independently alkyl, j is 1, and k is 1.

14. The semiconductor composition of claim 12, wherein the polymer binder is a styrene-based polymer or an arylamine-based polymer.

15. The semiconductor composition of claim 1, wherein the weight ratio of the small molecule semiconductor of Formula (I) to the polymer binder is from about 5:1 to about 2:3, and the total amount of the small molecule semiconductor and the polymer binder is from about 0.1 to about 10 weight percent of the semiconductor composition.

16. The semiconductor composition of claim 1, wherein the small molecule semiconductor has the structure of Formula (V):

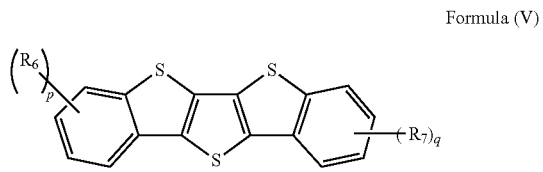

Formula (V)

wherein $R_6$ and $R_7$ are independently selected from alkyl, substituted alkyl, alkenyl, substituted alkenyl, alkynyl, substituted alkynyl, aryl, substituted aryl, heteroaryl, substituted heteroaryl, alkoxy, alkylthio, trialkylsilyl, ketonyl, cyano, and halogen; and p and q are independently an integer from 0 to 4.

17. The semiconductor composition of claim 1, wherein the small molecule semiconductor has the structure of Formula (VI):

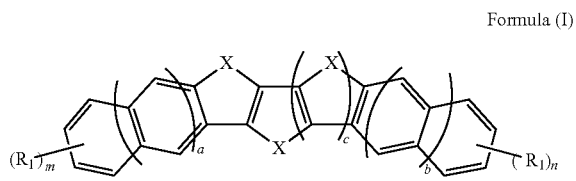

Formula (VI)

wherein $R_{10}$ and $R_{11}$ are independently selected from alkyl, substituted alkyl, alkenyl, substituted alkenyl, alkynyl, substituted alkynyl, aryl, substituted aryl, heteroaryl, substituted heteroaryl, alkoxy, alkylthio, trialkylsilyl, ketonyl, cyano, and halogen; and a, b, and c are independently 0 or 1.

18. A process for making a semiconducting layer of an electronic device, comprising:
depositing upon a surface a composition comprising a polymer binder and a small molecule semiconductor of Formula (I):

Formula (I)

wherein each $R_1$ is independently selected from alkyl, substituted alkyl, alkenyl, substituted alkenyl, alkynyl, substituted alkynyl, aryl, substituted aryl, heteroaryl, substituted heteroaryl, alkoxy, alkylthio, trialkylsilyl, ketonyl, cyano, and halogen; m and n are the number of R1 sidechains on their respective phenyl or naphthyl ring, and are independently an integer from 0 to 6; X is selected from the group consisting of O, S, and Se; and a, b and c are independently 0 or 1; and
drying the composition at a temperature below the melting point of the small molecular semiconductor; and
optionally annealing the composition at a temperature below the melting point of the small molecular semiconductor to form the semiconducting layer;
wherein the semiconducting layer has a mobility of at least 0.10 cm$^2$/V·sec.

19. An electronic device comprising a semiconducting layer, wherein the semiconductor layer comprises a polymer binder and a small molecule semiconductor of Formula (I):

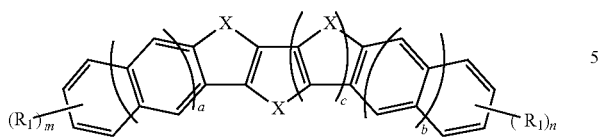

Formula (I)

wherein each $R_1$ is independently selected from alkyl, substituted alkyl, alkenyl, substituted alkenyl, alkynyl, substituted alkynyl, aryl, substituted aryl, heteroaryl, substituted heteroaryl, alkoxy, alkylthio, trialkylsilyl, ketonyl, cyano, and halogen; m and n are the number of R1 sidechains on their respective phenyl or naphthyl ring, and are independently an integer from 0 to 6; X is selected from the group consisting of O, S, Se; and a, b and c are independently 0 or 1; and wherein the semiconducting layer has a field-effect mobility of at least 0.10 cm$^2$/V·sec.

20. The electronic device of claim 19, wherein the electronic device further comprises a dielectric layer having a modified surface in contact with the semiconductor layer which has been modified with a polystyrene, a polysiloxane, a polysilsesquioxane, or an organosilane agent of Formula (A):

Formula (A)

wherein R is hydrocarbon or fluorocarbon containing from 1 to about 20 carbon atoms, R" is halogen or alkoxy; and m is an integer from 1 to 4.

* * * * *